(12) United States Patent
Peet

(10) Patent No.: US 12,636,180 B2
(45) Date of Patent: May 26, 2026

(54) OSTOMY BAG FILTER

(71) Applicant: Donaldson Company, Inc.,
Bloomington, MN (US)

(72) Inventor: Roger E. Peet, Eden Prairie, MN (US)

(73) Assignee: Donaldson Company, Inc.,
Bloomington, MN (US)

( * ) Notice: Subject to any disclaimer, the term of this
patent is extended or adjusted under 35
U.S.C. 154(b) by 849 days.

(21) Appl. No.: 17/915,418

(22) PCT Filed: Mar. 26, 2021

(86) PCT No.: PCT/US2021/024509
§ 371 (c)(1),
(2) Date: Sep. 28, 2022

(87) PCT Pub. No.: WO2021/202314
PCT Pub. Date: Oct. 7, 2021

(65) Prior Publication Data
US 2023/0137568 A1 May 4, 2023

Related U.S. Application Data

(60) Provisional application No. 63/002,027, filed on Mar.
30, 2020.

(51) Int. Cl.
*A61F 5/441* (2006.01)
*A61F 5/445* (2006.01)
(Continued)

(52) U.S. Cl.
CPC .......... *A61F 5/441* (2013.01); *B01D 39/1623*
(2013.01); *A61F 5/445* (2013.01); *A61F 5/448*
(2013.01)

(58) Field of Classification Search
CPC .......... A61F 5/441; A61F 5/448; A61F 5/445;
B01D 39/1623
See application file for complete search history.

(56) References Cited

U.S. PATENT DOCUMENTS 3,952,727 A     4/1976 Nolan
4,120,715 A *  10/1978 Ockwell ................ B32B 3/266
                                                      156/289
(Continued)

FOREIGN PATENT DOCUMENTS

CN        102933180      2/2013
EP        0358316         3/1990
(Continued)

OTHER PUBLICATIONS

"Non-Final Office Action," for U.S. Appl. No. 18/087,394 mailed
Jul. 27, 2023 (26 pages).
(Continued)

*Primary Examiner* — Guy K Townsend
(74) *Attorney, Agent, or Firm* — Pauly, DeVries Smith &
Deffner LLC

(57) ABSTRACT

Embodiments herein relate to an ostomy bag filter. In an
embodiment, a filter assembly for venting gas from an
ostomy bag is included having a first layer, an adhesive
layer, an adsorbent element, and a second layer, the second
layer configured to be welded to the ostomy bag at an
annular weld area surrounding the second opening; wherein
the adhesive layer is configured to adhere to the first layer,
the adsorbent element, and the second layer, such that the
first opening overlaps with the second opening; wherein the
filter assembly is configured such that, when the filter
assembly is welded over to the ostomy bag, gas from the
ostomy bag flows axially through the adsorbent element and
exits the filter assembly through the second opening; and
wherein perimeters of the first layer, the adhesive layer, and
the second layer are substantially aligned. Other embodi-
ments are also included herein.

14 Claims, 15 Drawing Sheets

(51) Int. Cl.
　　*A61F 5/448*　　　(2006.01)
　　*B01D 39/16*　　　(2006.01)

(56)　　　　　References Cited

U.S. PATENT DOCUMENTS

| | | | |
|---|---|---|---|
| 4,203,445 A | 5/1980 | Jessup et al. | |
| 4,274,848 A | 6/1981 | La Gro | |
| 4,318,406 A | 3/1982 | McLeod | |
| 4,372,308 A | 2/1983 | Steer et al. | |
| 4,395,332 A | 7/1983 | Klein | |
| 4,460,392 A | 7/1984 | Poulsen et al. | |
| 4,490,145 A | 12/1984 | Campbell et al. | |
| 4,668,258 A | 5/1987 | Steer | |
| 4,723,951 A | 2/1988 | Steer | |
| 4,917,689 A | 4/1990 | Coombes et al. | |
| 4,957,522 A * | 9/1990 | Brassell | B01D 39/14 |
| | | | 55/385.4 |
| 5,074,851 A | 12/1991 | Plass et al. | |
| 5,085,652 A | 2/1992 | Johnsen et al. | |
| 5,207,970 A | 5/1993 | Joseph et al. | |
| 5,250,042 A | 10/1993 | Torgalkar et al. | |
| 5,304,157 A | 4/1994 | Brooks et al. | |
| 5,306,264 A * | 4/1994 | Ferguson | A61F 5/441 |
| | | | 604/338 |
| 5,417,678 A * | 5/1995 | Baumann | A61F 5/441 |
| | | | 604/333 |
| 5,549,587 A | 8/1996 | Norton | |
| 5,591,144 A | 1/1997 | Shelley et al. | |
| 5,643,234 A | 7/1997 | Lesko | |
| 5,690,622 A | 11/1997 | Smith et al. | |
| 5,952,422 A | 9/1999 | Chang et al. | |
| 6,120,536 A | 9/2000 | Ding et al. | |
| 6,129,716 A | 10/2000 | Steer et al. | |
| 6,135,986 A * | 10/2000 | Leisner | A61F 5/441 |
| | | | 604/324 |
| 6,241,712 B1 | 6/2001 | Steer et al. | |
| 6,359,100 B1 | 3/2002 | Hostettler et al. | |
| 6,506,184 B1 * | 1/2003 | Villefrance | A61F 5/441 |
| | | | 604/333 |
| 6,659,988 B1 * | 12/2003 | Steer | A61F 5/441 |
| | | | 604/335 |
| 6,695,826 B2 * | 2/2004 | Villefrance | A61F 5/441 |
| | | | 604/333 |
| 6,723,428 B1 | 4/2004 | Foss et al. | |
| 6,773,420 B2 | 8/2004 | Kanbara | |
| 6,946,196 B2 | 9/2005 | Foss | |
| 7,160,275 B2 | 1/2007 | Falconer | |
| 7,214,217 B2 | 5/2007 | Pedersen et al. | |
| 7,326,190 B2 | 2/2008 | Botten | |
| 7,341,578 B2 * | 3/2008 | Bulow | A61F 5/441 |
| | | | 604/338 |
| 7,604,622 B2 | 10/2009 | Pedersen et al. | |
| 7,655,070 B1 | 2/2010 | Dallas et al. | |
| 8,048,210 B2 | 11/2011 | Dallas et al. | |
| 8,211,218 B2 | 7/2012 | Dallas et al. | |
| 8,246,730 B2 | 8/2012 | Dallas et al. | |
| 8,343,264 B2 | 1/2013 | Dallas et al. | |
| 8,585,753 B2 | 11/2013 | Scanlon et al. | |
| 8,753,438 B2 | 6/2014 | Dallas et al. | |
| 8,979,811 B2 * | 3/2015 | Keleny | B01D 46/02 |
| | | | 604/338 |
| 9,028,858 B2 | 5/2015 | Nielsen et al. | |
| 9,168,180 B2 | 10/2015 | Ha et al. | |
| 9,539,137 B2 | 1/2017 | Smith | |
| 9,610,523 B2 | 4/2017 | Dallas et al. | |
| 9,833,352 B2 | 12/2017 | Maidl et al. | |
| 10,058,807 B2 | 8/2018 | Dallas et al. | |
| 10,646,370 B2 * | 5/2020 | Keleny | A61F 13/0008 |
| 11,344,835 B2 * | 5/2022 | Peet | B01D 63/08 |
| 11,534,324 B2 * | 12/2022 | Keleny | A61F 13/0008 |
| 11,925,573 B2 | 3/2024 | Keleny et al. | |
| 12,233,001 B2 | 2/2025 | Keleny et al. | |
| 2003/0100870 A1 * | 5/2003 | Villefrance | A61F 5/441 |
| | | | 604/333 |
| 2003/0170453 A1 | 9/2003 | Foss et al. | |
| 2003/0187412 A1 | 10/2003 | Martin et al. | |
| 2004/0089640 A1 | 5/2004 | Bager et al. | |
| 2004/0209059 A1 | 10/2004 | Foss | |
| 2004/0214495 A1 | 10/2004 | Foss et al. | |
| 2005/0003728 A1 | 1/2005 | Foss | |
| 2005/0070863 A1 * | 3/2005 | Bulow | A61F 5/441 |
| | | | 604/338 |
| 2005/0143696 A1 | 6/2005 | Pedersen et al. | |
| 2007/0049880 A1 * | 3/2007 | Suehr | A61F 5/441 |
| | | | 604/333 |
| 2007/0203466 A1 | 8/2007 | Pedersen et al. | |
| 2007/0207186 A1 | 9/2007 | Scanlon et al. | |
| 2008/0041229 A1 * | 2/2008 | Mathieu | A61F 5/441 |
| | | | 96/6 |
| 2009/0247970 A1 * | 10/2009 | Keleny | B01D 46/0036 |
| | | | 156/247 |
| 2010/0010460 A1 | 1/2010 | Butler | |
| 2010/0145291 A1 | 6/2010 | Kambara | |
| 2010/0247925 A1 | 9/2010 | Nielsen et al. | |
| 2010/0318052 A1 | 12/2010 | Ha et al. | |
| 2011/0112492 A1 | 5/2011 | Bharti et al. | |
| 2011/0212090 A1 | 9/2011 | Pedersen et al. | |
| 2011/0238024 A1 | 9/2011 | Smith et al. | |
| 2013/0317405 A1 | 11/2013 | Ha et al. | |
| 2015/0250931 A1 | 9/2015 | Bharti et al. | |
| 2016/0038345 A1 | 2/2016 | Ha et al. | |
| 2016/0235581 A1 * | 8/2016 | Keleny | A61F 13/0008 |
| 2017/0143533 A1 | 5/2017 | Schertiger et al. | |
| 2018/0250155 A9 * | 9/2018 | Keleny | A61F 13/0008 |
| 2019/0328581 A1 | 10/2019 | Doshi et al. | |
| 2020/0061511 A1 * | 2/2020 | Peet | B01D 69/1216 |
| 2020/0405522 A1 * | 12/2020 | Keleny | A61F 5/441 |
| 2023/0225896 A1 * | 7/2023 | Keleny | A61F 5/441 |
| | | | 604/333 |
| 2024/0293251 A1 * | 9/2024 | Keleny | A61F 13/0008 |
| 2025/0161097 A1 * | 5/2025 | Keleny | A61F 13/0008 |

FOREIGN PATENT DOCUMENTS

| | | |
|---|---|---|
| EP | 0235928 | 4/1991 |
| EP | 0607028 | 7/1994 |
| EP | 0680295 | 8/1999 |
| EP | 1198338 | 12/2003 |
| EP | 0981311 | 8/2004 |
| EP | 1514528 | 3/2005 |
| EP | 1875884 | 3/2011 |
| EP | 2494944 | 9/2012 |
| EP | 2274068 | 1/2016 |
| EP | 3096718 | 8/2020 |
| GB | 2059797 | 4/1981 |
| GB | 2276324 | 9/1994 |
| GB | 2287193 | 9/1995 |
| GB | 2291364 | 1/1996 |
| GB | 2302028 | 8/1997 |
| GB | 2510563 | 8/2014 |
| GB | 2549060 | 10/2017 |
| GB | 2528305 | 1/2019 |
| JP | 4571265 | 8/2010 |
| NO | 994883 | 12/1999 |
| WO | 0105573 | 1/2001 |
| WO | 2007030703 | 3/2007 |
| WO | 2007095363 | 8/2007 |
| WO | 2009146076 | 12/2009 |
| WO | 2019120431 | 6/2019 |
| WO | 2019120438 | 6/2019 |
| WO | 2019120439 | 6/2019 |
| WO | 2021202314 | 10/2021 |

OTHER PUBLICATIONS

File History for European Patent Application No. 16150548.2 downloaded Oct. 18, 2022 (320 pages).
File History for European Patent Application No. 09755439.8 downloaded Oct. 18, 2022 (879 pages).
File History for U.S. Patent Application No. downloaded Oct. 18, 2022 (740 pages).

(56)                References Cited

OTHER PUBLICATIONS

File History for U.S. Appl. No. 16/870,578 downloaded Oct. 18, 2022 (189 pages).
File History for U.S. Appl. No. 12/414,951 downloaded Oct. 18, 2022 (348 pages).
"Decision on Reexamination," for Chinese Patent Application No. 200980112883.2, mailed Sep. 30, 2015 (10 pages).
"Decision on Rejection," for CN Application No. 200980112883.2, mailed Apr. 11, 2014 (19 pages).
"First Office Action," First Office Action from CN Application No. 200980112883.2 mailed Jan. 28, 2013, 24 pages, including English translation.
"International Preliminary Report on Patentability," for PCT Application No. PCT/US2021/024509 mailed Oct. 13, 2022 (8 pages).
"International Preliminary Report on Patentability," for PCT Application No. PCTUS09/039148 mailed Oct. 14, 2010 (6 pages).
"International Search Report and Written Opinion," for PCT Application No. PCT/US2021/024509 mailed Jul. 8, 2021 (11 pages).
"PCT International Search Report and Written Opinion from International Application No. PCT/US2009/039148, corresponding to U.S. Appl. No. 12/414,951, mailed Nov. 24, 2009, pp. 1-11".
"Second Office Action," for Chinese Application No. 200980112883.2, mailed Sep. 23, 2013 (16 pages) with English Translation.
"Third Office Action," for Chinese Patent Application No. 200980112883.2, mailed Dec. 18, 2015 (8 pages) with translation.
"Non-Final Office Action," for U.S. Appl. No. 18/599,903 mailed Sep. 18, 2024 (29 pages).
"Notice of Allowance," for U.S. Appl. No. 18/087,394 mailed Nov. 7, 2023 (14 pages).
"Notice of Allowance," for U.S. Appl. No. 18/599,903 mailed Dec. 29, 2024 (14 pages).
"Response to Non Final Office Action," for U.S. Appl. No. 18/599,903, filed Nov. 27, 2024 (6 pages).
"Office Action," for Chinese Patent Application No. 202180023669.0 mailed May 12, 2025 (32 pages) with English translation.
"Response to Rule 161(1) and 162 Communication," for European Patent Application No. 21720089.8 filed Apr. 24, 2023 (16 pages).

* cited by examiner

200

202

4                                                    4

200

204

306

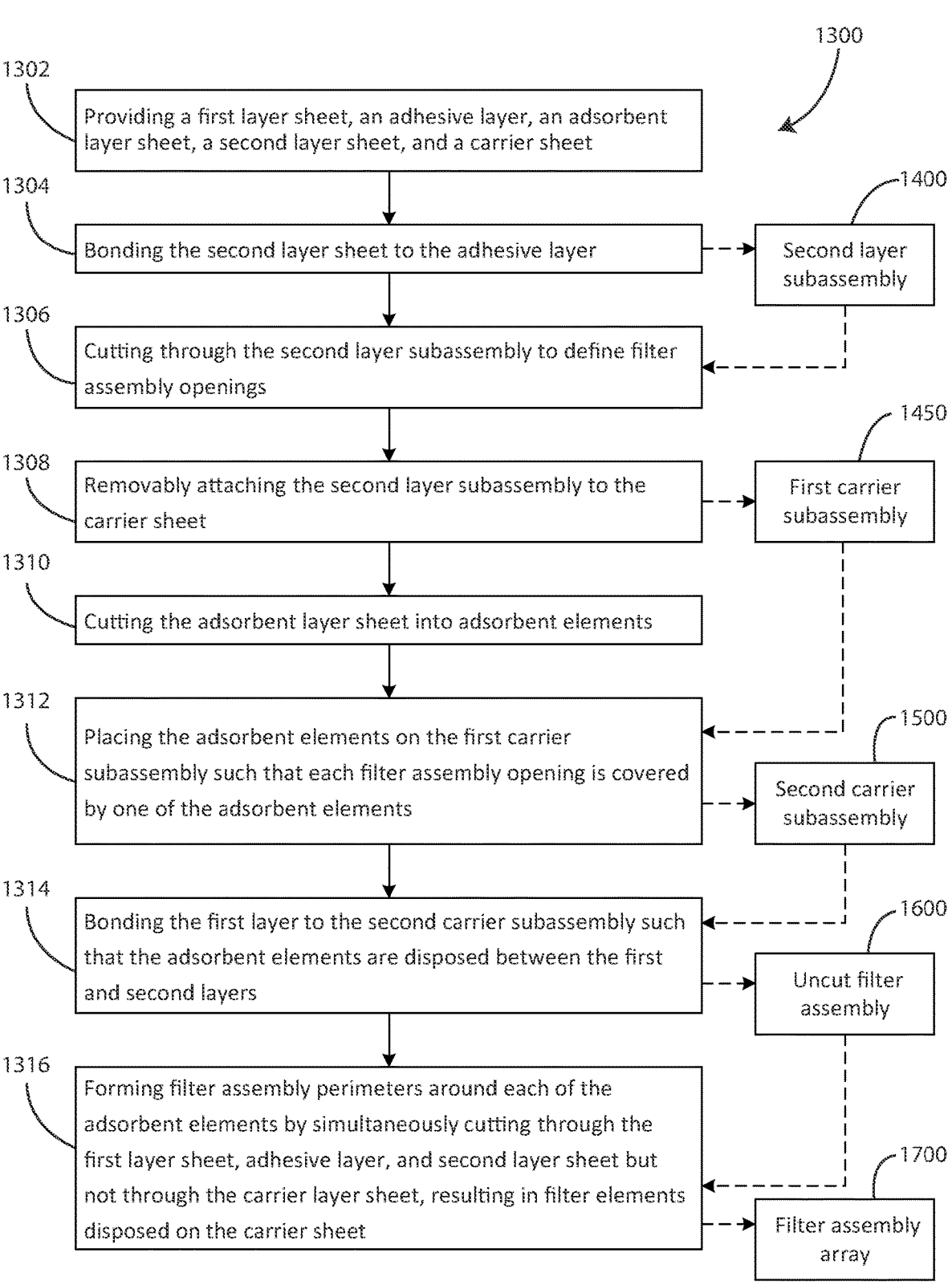

1300

1302 Providing a first layer sheet, an adhesive layer, an adsorbent layer sheet, a second layer sheet, and a carrier sheet 1304 Bonding the second layer sheet to the adhesive layer — → 1400 Second layer subassembly 1306 Cutting through the second layer subassembly to define filter assembly openings 1308 Removably attaching the second layer subassembly to the carrier sheet — → 1450 First carrier subassembly 1310 Cutting the adsorbent layer sheet into adsorbent elements 1312 Placing the adsorbent elements on the first carrier subassembly such that each filter assembly opening is covered by one of the adsorbent elements — → 1500 Second carrier subassembly 1314 Bonding the first layer to the second carrier subassembly such that the adsorbent elements are disposed between the first and second layers — → 1600 Uncut filter assembly 1316 Forming filter assembly perimeters around each of the adsorbent elements by simultaneously cutting through the first layer sheet, adhesive layer, and second layer sheet but not through the carrier layer sheet, resulting in filter elements disposed on the carrier sheet — → 1700 Filter assembly array

FIG. 12

OSTOMY BAG FILTER

CROSS-REFERENCE TO RELATED APPLICATIONS

This application is a 35 U.S.C. § 371 national phase application of PCT Application No. PCT/US2021/024509 (WO 2021/202314A1), filed on Mar. 26, 2021, which claims the benefit of U.S. Provisional Application No. 63/002,027, filed on Mar. 30, 2020, each of which is incorporated herein by reference in its entirety.

FIELD

The present invention relates to adsorbent breather filters for enclosures, such as bags, and more particularly ostomy bags, and more particularly, to ventilation filters and assemblies for ostomy bags.

BACKGROUND

An ostomy (also referred to as a colostomy, ileostomy or urostomy) is a type of surgery required when a person loses normal bladder or bowel function due to birth defect, disease, injury, or other disorder. Cancer patients account for about 80 percent of ostomies. Following an ostomy, bodily waste needs to be expelled through a stoma (surgical opening) on the abdominal wall and into a special appliance called an ostomy bag.

Depending on a patient's diet, age, diagnosis, activity level, and other variables, these wastes can contain significant amounts of gases, such as amines, ammonia, and mercaptans. These gases can inflate the ostomy bag, creating concern or discomfort for the patient and compromise the seal between the skin and the bag itself.

In the past, ostomy bags have been provided with deodorizing gas filters so that flatus gases can be vented from the bag to reduce or prevent ballooning and, at the same time, to deodorize the escaping gases. In an effort to prevent such a filter from becoming clogged and rendered ineffective by liquid and/or solid body waste material within the bag, it has been common either to secure the filter to the outside surface of the bag over a vent opening, or to provide protection for an internally mounted filter in the form of a porous membrane that extends over the filter. Typically, this membrane over an internally mounted filter is hydrophobic and may also be oleophobic.

Ostomy bag filters may be of the axial flow type, or more commonly the so-called radial flow type or lateral flow type. These and other flow path types are described in commonly owned U.S. Pat. No. 8,979,811, issued on Mar. 17, 2015, which is incorporated herein by reference in its entirely. For ostomy bag applications, a filter of the radial or lateral flow type is most common because it allows for the construction of a low-profile filter that also provides a longer flow path for deodorizing the flatus gases.

SUMMARY

In an embodiment, a filter assembly for venting gas from an ostomy bag is included having a first layer configured to be gas permeable and liquid impermeable, an adhesive layer defining at least a first opening, an adsorbent element can include a gas-adsorbing material, the adsorbent element disposed between the first layer and the adhesive layer, and a second layer can include a material having a melt temperature at or below 120° C. and defining at least a second opening, the second layer configured to be welded to the ostomy bag at an annular weld area surrounding the second opening, wherein the adhesive layer is configured to adhere to the first layer, the adsorbent element, and the second layer, such that the first opening overlaps with the second opening, wherein the filter assembly is configured such that, when the filter assembly is welded over an exit opening of the ostomy bag, gas from within the ostomy bag flows axially through the adsorbent element and exits the filter assembly through the second opening, and wherein perimeters of the first layer, the adhesive layer, and the second layer are substantially aligned.

In an embodiment, the first layer can include polytetrafluoroethylene (PTFE).

In an embodiment, the first layer can include a PTFE laminate.

In an embodiment, the adhesive layer can include a double-sided adhesive laminate.

In an embodiment, the adhesive layer can include a pressure sensitive adhesive.

In an embodiment, the adhesive layer is a coating on the second layer.

In an embodiment, the adsorbent element can include activated carbon.

In an embodiment, the second layer can include ethylene-vinyl acetate (EVA), polyethylene (PE), or polypropylene (PP).

In an embodiment, the first and second openings overlap at least about 70% of a length of the adsorbent element.

In an embodiment, the first and second openings overlap at least about 25% of an area of one side of the adsorbent element.

In an embodiment, the adhesive layer further defines a third opening and the second layer further defines a fourth opening that overlaps with the third opening.

In an embodiment, the overlapped first and second opening define a first filter assembly opening, wherein the overlapped third and fourth openings define a second filter assembly opening, and wherein the first and second filter assembly openings are substantially equal in area.

In an embodiment, a array of filter assemblies is included having a plurality of filter assemblies, each filter assembly is included having a first layer configured to be gas permeable and liquid impermeable, an adhesive layer defining a first opening, an adsorbent element can include a gas-adsorbing material, the adsorbent element disposed between the first layer and the adhesive layer, and a second layer can include a material having a melt temperature at or below 120° C. and defining a second opening, the second layer configured to be welded to an ostomy bag at an annular weld area surrounding the second opening, and a carrier can include a carrier adhesive disposed on a first side of the carrier, wherein each of the filter assemblies is removably attached to the first side of the carrier.

In an embodiment, the carrier adhesive includes a low-tack adhesive.

In an embodiment, the carrier is wound into a filter assembly supply roll.

In an embodiment, wherein each of the plurality of filter assembly is configured such that, when the filter assembly is welded over an exit opening of the ostomy bag, gas from within the ostomy bag flows axially through the adsorbent element and exits the filter assembly through the second opening.

In an embodiment, further can include a gas-impermeable barrier layer positioned between the first layer and the adsorbent element configured to obstruct the flow of gas through the filter assembly from the direction of a first side of the adsorbent element, wherein each of the plurality of filter assembly is configured such that, when the filter assembly is welded over an exit opening of the ostomy bag, gas from within the ostomy bag flows laterally through the adsorbent element and exits the filter assembly through the second opening.

In an embodiment, the first layer can include polytetrafluoroethylene (PTFE).

In an embodiment, the first layer can include a PTFE laminate.

In an embodiment, the adhesive layer can include a double-sided adhesive laminate.

In an embodiment, the adhesive layer can include a pressure sensitive adhesive.

In an embodiment, the adhesive layer is a coating on the second layer.

In an embodiment, the adsorbent element can include activated carbon.

In an embodiment, the second layer can include ethylene-vinyl acetate (EVA), polyethylene (PE), or polypropylene (PP).

In an embodiment, the first and second openings overlap at least about 70% of a length of the adsorbent element.

In an embodiment, the first and second openings overlap at least about 25% of an area of one side of the adsorbent element.

In an embodiment, the adhesive layer further defines a third opening and the second layer further defines a fourth opening that overlaps with the third opening.

In an embodiment, the overlapped first and second opening define a first filter assembly opening, wherein the overlapped third and fourth openings define a second filter assembly opening, and wherein the first and second filter assembly openings are substantially equal in area.

In an embodiment, a method of producing a filter assembly is included, the method providing sheets of a first layer, an adhesive layer, an adsorbent layer, a second layer, and a carrier layer, wherein: the first layer is configured to be gas permeable and liquid impermeable, the adsorbent layer includes a gas-adsorbing material, the second layer includes a material having a melt temperature at or below 120° C., and the carrier layer includes a carrier adhesive disposed on an adhesive side of the carrier, bonding the second layer to the adhesive layer, simultaneously cutting through the second layer and adhesive layer to form an opening, removably attaching the second layer to an adhesive side of the carrier layer, cutting the adsorbent layer into discrete adsorbent elements, placing one of the discrete adsorbent elements to cover the opening of the adhesive layer, bonding the first layer to the adhesive layer, such that the adsorbent element is disposed between the first and second layers, and forming a perimeter around the adsorbent element by simultaneously cutting through the first layer, adhesive layer, and second layer resulting in a filter element disposed on the carrier layer.

In an embodiment, a method of producing a plurality of filter assemblies is included, the method providing a first layer sheet, an adhesive layer, an adsorbent layer sheet, a second layer sheet, and a carrier sheet, wherein: the first layer sheet is configured to be gas permeable and liquid impermeable, the adsorbent layer sheet includes a gas-adsorbing material, the second layer sheet includes a material having a melt temperature at or below 120° C., and the carrier sheet includes a carrier adhesive disposed on an adhesive side of the carrier, bonding the second layer sheet to the adhesive layer to form a second layer subassembly having a first side and an opposite adhesive layer side, cutting through the second layer subassembly to define a plurality of filter assembly openings in the second layer subassembly, removably attaching the first side of the second layer subassembly to the adhesive side of the carrier sheet to form a first carrier subassembly having a first side and an opposite adhesive layer side, cutting the adsorbent layer sheet into a plurality of adsorbent elements, placing the plurality of adsorbent elements on the adhesive layer side of the first carrier subassembly such that each of the plurality of filter assembly openings is covered by one of the plurality of adsorbent elements, thereby forming a second carrier subassembly having a first side and an adhesive layer side, bonding the first layer to the adhesive layer side of the second carrier subassembly such that the adsorbent elements are disposed between the first and second layers to form an uncut filter assembly, and forming a plurality of filter assembly perimeters around each of the adsorbent elements by simultaneously cutting through the first layer sheet, adhesive layer, and second layer sheet but not through the carrier layer sheet, resulting in a plurality of filter elements disposed on the carrier layer sheet.

In an embodiment, the method can further include winding the plurality of filter elements disposed on the carrier layer into a filter element supply roll.

In an embodiment, the adhesive layer includes a pressure sensitive adhesive and winding of the plurality of filter elements disposed on the carrier layer into the filter element supply roll compresses the first layer sheet, adhesive layer, and second layer sheet.

In an embodiment, the method can further include unwinding the second layer sheet from a second layer supply roll, wherein the second layer sheet on the second layer supply roll includes the adhesive layer on an adhesive layer side.

In an embodiment, the method can further include forming the second layer subassembly at least 24 hours before forming the plurality of filter assembly perimeters.

In an embodiment, the method can further include forming the plurality of filter assembly perimeters at least 24 hours before applying a filter element of the plurality of filter elements to an ostomy bag.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 12 is flowchart of a method of manufacturing filter assemblies according to various embodiments herein.

Figure 1:
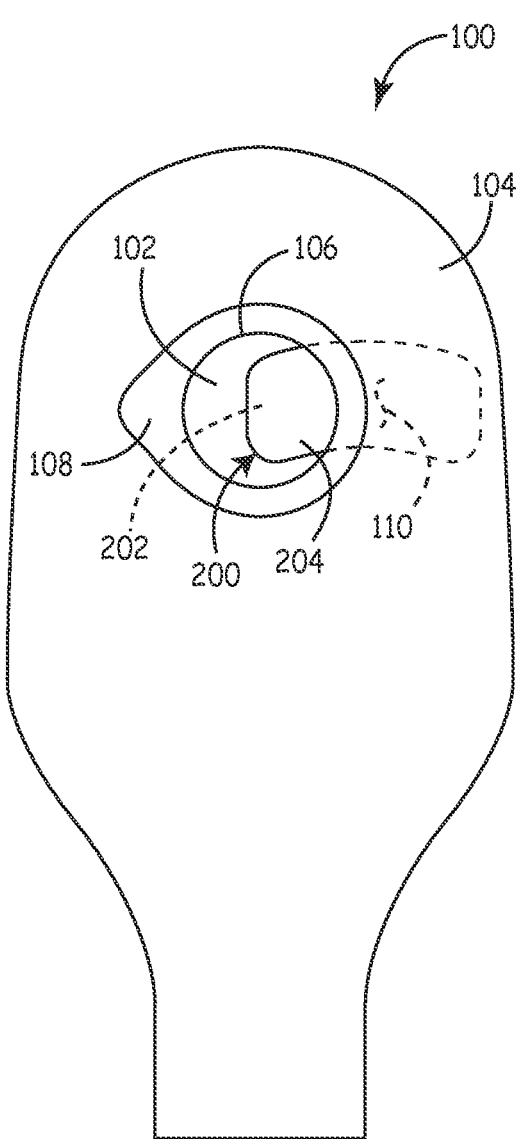
FIG. 1 is a top view of an ostomy bag having a filter assembly according to various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

A filter assembly is described herein including, in certain embodiments, a filter layer including adsorbent material, plus at least one outer, gas permeable film layer, which will be referred to as a first layer. The first layer is heat sealable in some embodiments and is microporous in some embodiments. The filter assembly has a low profile and is capable of selective gas adsorption, absorption, catalysis, or combination of each. This type of filter assembly can be placed over a vent as a vent assembly and is often referred to as an Adsorbent Breather Filter (ABF).

ABFs are most commonly used to seal a breather hole in liquid tight enclosures. Vented ostomy bags, where liquid and solid phase materials are trapped while select gases are allowed to escape, is an example where the filter assembly described herein is particularly useful. ABFs are also commonly used in sensor and electronic enclosures where the focus is on keeping solids and liquids outside the enclosure while allowing select gas phase fluid to enter for cooling and/or sensing purposes.

The filter assembly can be used with many different types of enclosures, both flexible and rigid. In one embodiment, the enclosure is a bag, which is a flexible enclosure made mostly of plastic. The filter assembly is particularly useful in the context of its use with an ostomy bag, and it will be described herein in that context for convenience. The filter assembly has two sides: a bag side or enclosure side to be sealed to an ostomy bag or other enclosure, and an outer side opposite from the bag side. For convenience, the enclosure side of the filter assembly will be referred to as the bag side herein, and the filter assembly will generally be discussed in the context of an enclosure bag, specifically, an ostomy bag, although the concepts herein are equally applicable to other types of enclosures.

The filter assemblies described herein have been engineered to eliminate unnecessary components from prior art arrangements, reduce the cost of the filter assembly, and provide full functionality to the end user, as well as provide features used during the ostomy bag manufacturing process. Compared to previous designs that include an expanded polytetrafluoroethylene (ePTFE) laminate on the bag side of the filter assembly, the filter assembly described herein may also reduce the tendency of fecal matter to plug the filter and thereby improve the useful life of the filter. Elimination of an ePTFE laminate on the bag side also reduces the cost of the filter assembly.

Filter Assembly

Figure 2:
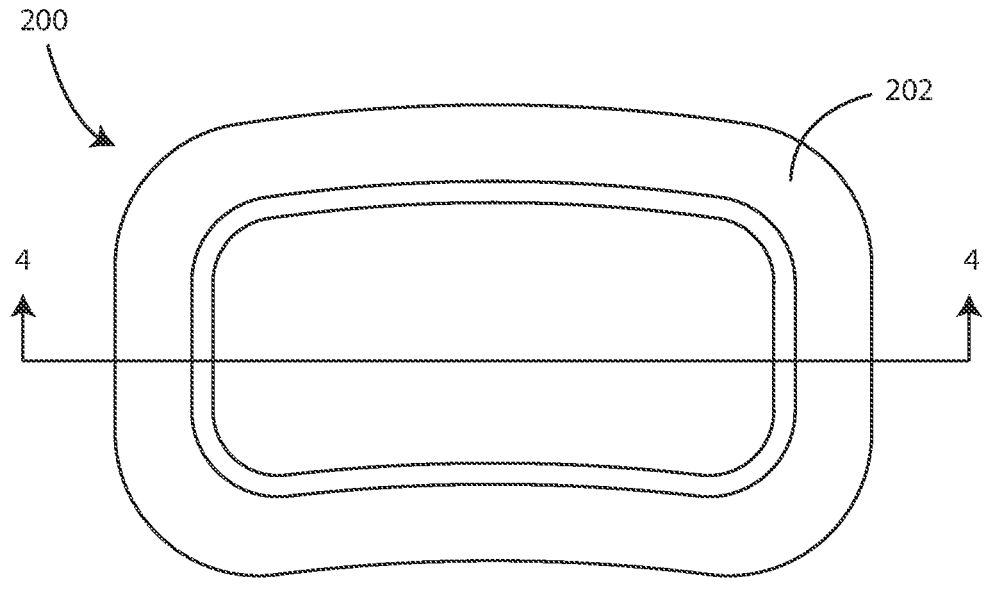
FIG. 2 is a top plan view of a first side of a filter assembly according to one embodiment.
Figure 3:
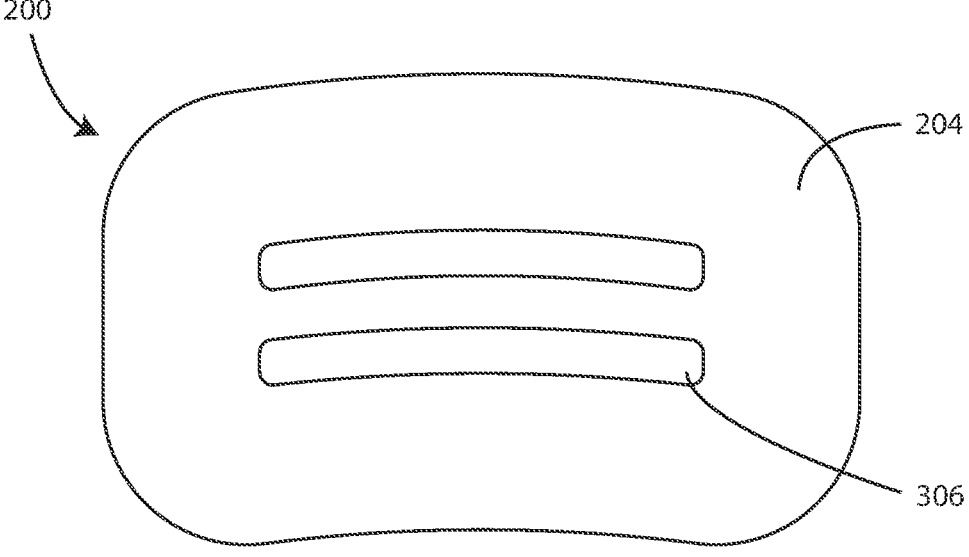
FIG. 3 is a bottom plan view of a second side the filter assembly of FIG. 2 according to various embodiments herein.

Referring now to FIGS. 1-3, a top view of an ostomy bag having a filter assembly is shown in FIG. 1 and top and bottom views of the filter assembly are shown in FIGS. 2 and 3, respectively, according to various embodiments herein. The ostomy bag 100 includes an interior surface 102, an exterior surface 104, and a stoma opening 106 into an interior of the ostomy bag. The stoma opening 106 is surrounded by a flange 108, which is where the ostomy bag will be connected to the user's stoma. The ostomy bag 100 also defines a vent opening 110. A filter assembly 200 can be secured to an interior side of the ostomy bag 100, so that the filter covers the vent opening 110. The outline of the filter assembly 200 is visible through the stoma opening 106 and is shown in dashed lines where it is hidden by a top layer of the ostomy bag. The filter assembly 200 can have a second layer 204 that is secured to the bag, and a first layer 202, which is opposite to the second layer. The second layer 204 is visible in FIG. 1 through the stoma opening, as well as in FIG. 3, while FIG. 2 is a bottom plan view of the filter assembly showing second layer 204.

The filter assembly 200 can be of any shape that is compatible with the ostomy bag 100 and/or the body of a patient. In various embodiments the filter assembly 200 can be substantially rectangular in shape. In various embodiments, the filter assembly 200 can be rounded at the corners. In an embodiment, the filter assembly 200 is substantially rectangular in area with an opposing set of curved sides. In various embodiments, the top of the filter assembly 200 is formed by the first layer 202.

Referring now to FIG. 3, a bottom plan view of a second side the filter assembly of FIG. 2 is shown according to various embodiments herein. In various embodiments, the bottom of the filter assembly 200 is formed by the second layer 204. The second layer is configured to be bonded to an ostomy bag. In various embodiments, the outer perimeter of the second layer 204 is substantially aligned with the outer perimeter of the first layer 202. The filter assembly 200 can include one or more filter assembly openings 306 extending through the second layer 204 of the filter assembly.

Figure 4:
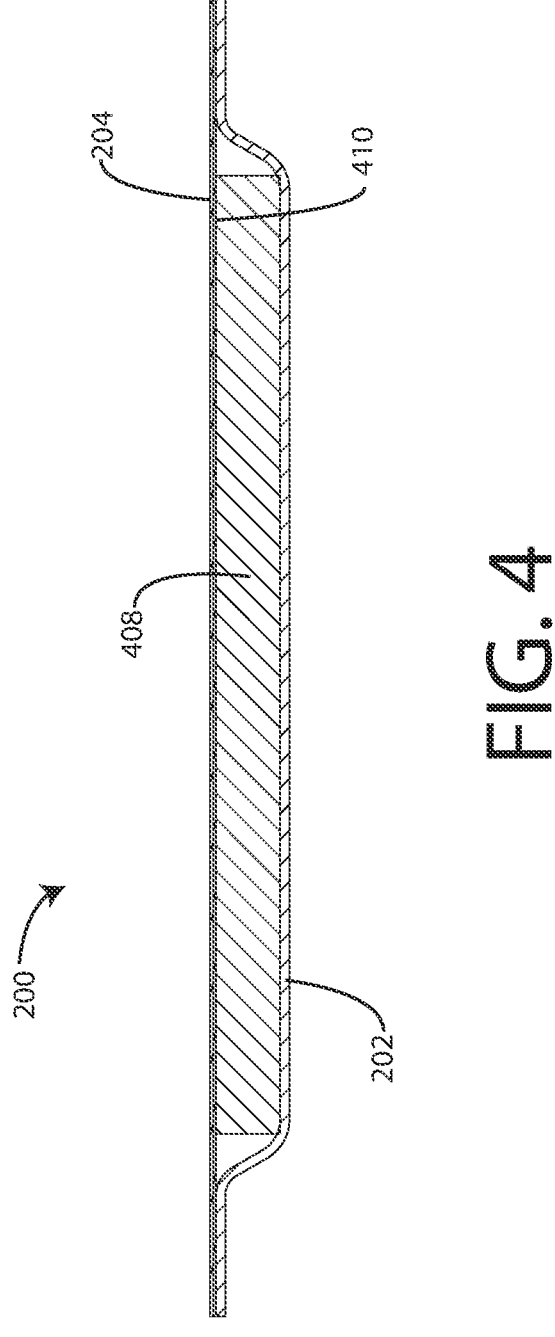
FIG. 4 is a cross-sectional view of the filter assembly of FIG. 2 through section line 4-4 of FIG. 2, according to various embodiments herein.

Referring now to FIG. 4, a cross-sectional view of the filter assembly of FIG. 2 through section line 4-4 is shown according to various embodiments herein. In various embodiments the filter assembly 200 can include a first layer 202, an adhesive layer 410, an adsorbent element 408, and a second layer 204. As seen in FIG. 4, the outer perimeters of the first layer 202, the adhesive layer 410, and the second layer 204 can substantially aligned. In an alternative embodiment, the second layer 204 can have a perimeter that fits within and is spaced away from the perimeter of the first layer 202.

Figure 5:
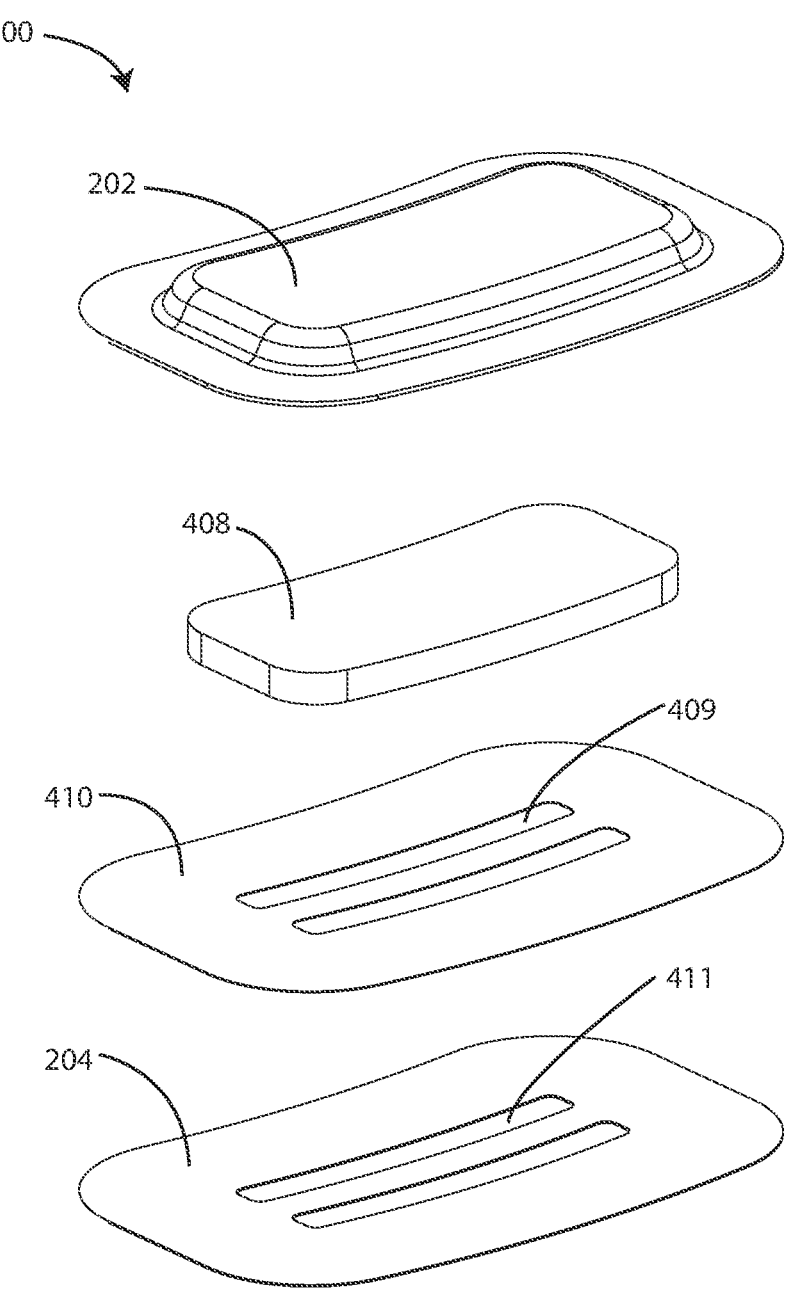
FIG. 5 is an exploded view of components of a filter assembly of FIG. 2, according to various embodiments herein.

Referring now to FIG. 5, an exploded view of components of the filter assembly of FIG. 2 is shown according to various embodiments herein. In various embodiments the filter assembly 200 can include a first layer 202, an adhesive layer 410, an adsorbent element 408, and a second layer 204. As shown in FIG. 5, the adhesive layer 410 can form a distinct layer of filter assembly 200. The adhesive layer can be disposed between the first layer and the adsorbent element when the filter assembly in in an assembled state. As shown in FIG. 5, the adhesive layer 410 can have at least a first opening 409 and the second layer 204 can have at least a second opening 411. In various embodiments, the first opening 409 and the second opening 411 at least partially overlap when the filter assembly 200 is in its assembled state and form at least one filter assembly opening 306.

Figure 6:
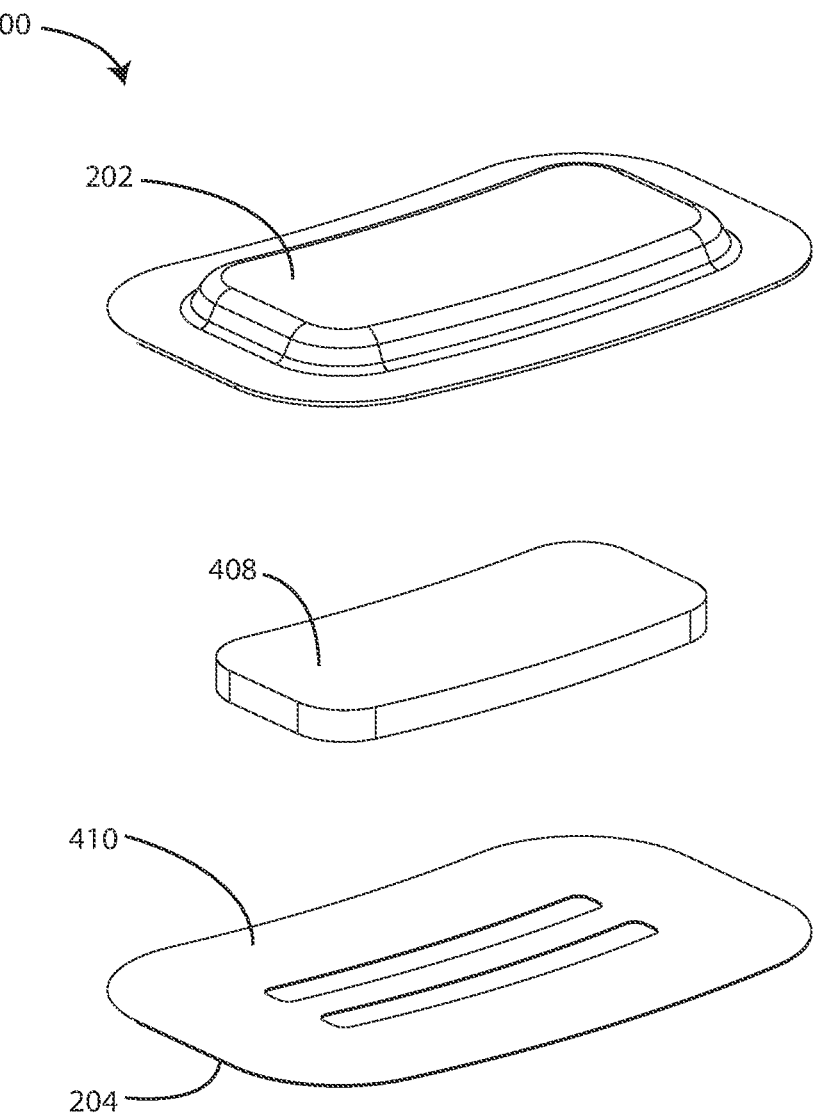
FIG. 6 is an exploded view of alternate components of a filter assembly of FIG. 2 according to with various embodiments herein.

Referring now to FIG. 6, an exploded view of components of the filter assembly of FIG. 2 is shown according to various embodiments herein. In various embodiments the filter assembly 200 can include a first layer 202, an adhesive layer 410, an adsorbent element 408, and a second layer 204. In some embodiments, the adhesive layer 410 can be integral with the second layer 204. As shown in FIG. 6, the second layer 204 can include an adhesive coating or adhesive layer 410 facing the adsorbent element 408.

First Layer

In various embodiments, the filter assembly 200 can include a first layer 202. In various embodiments, the first layer is configured to be gas permeable. The first layer can be microporous. The term "microporous" as used herein refers to a material containing pores with diameters of about 2 microns or less than 2 microns. In some embodiments, the first layer is also liquid impermeable. The first layer can include a number of materials including but not limited to polytetrafluoroethylene (PTFE), a layer only containing PTFE, a laminate including PTFE, and expanded PTFE, low density polyethylene (PE), polyolefin, or a porous membrane. In various embodiments, the first layer is sufficiently complaint to conform to the shape of the adsorbent element 408.

The first layer has a thickness of at least 0.013 mm in one embodiment, and at most 0.09 mm in one embodiment. In some embodiments, the thickness of the first layer 202 can be greater than or equal to 0.01 mm, 0.02 mm, 0.04 mm, or 0.05 mm. In some embodiments, the thickness can be less than or equal to 0.10 mm, 0.08 mm, 0.07 mm, or 0.05 mm. In some embodiments, the thickness can fall within a range of 0.01 mm to 0.10 mm, or 0.02 mm to 0.08 mm, or 0.04 mm to 0.07 mm, or can be about 0.05 mm Adsorbent Element In various embodiments, the filter assembly 200 can include an adsorbent element 408. In various embodiments, the adsorbent element can take the form of an adsorbent layer, adsorbent section, a piece of adsorbent material, an adsorbent sheet, or the like. In various embodiments, the adsorbent element includes a gas adsorbing material. One embodiment of the adsorbent element incorporates an activated carbon and fiber matrix containing finely divided activated carbon particles constrained by fine fibers, such as electrospun polymeric fine fibers. The activated carbon and fiber matrix is then laminated and/or encapsulated by various micro-porous and/or non-porous films to create a highly effective and low-profile ostomy vent capable of selective gas adsorption, catalysis, or combination of each.

In one embodiment, adsorbent material is suspended in a material web that k capable of roll-to-roll processing and manufacturing techniques. The term web is used to mean a thin, flexible material capable of being rolled, typically in a long format that is much longer in a machine direction than it is wide in a perpendicular, cross-machine direction.

In one embodiment, adsorbent material is suspended within a foam or felt material.

In one embodiment, the adsorbent material includes a scrim base layer upon which is formed a layer of adsorptive particles, such as carbon particles, and fibers, such as fine fibers. Additional layers of adsorptive particles and fibers are added to create the adsorbent material. In one embodiment, the scrim side of the adsorbent material faces the first layer.

The reactive or adsorptive particles are held together or interspersed with fibers. The combination of particles and fibers results in a material that offers several advantages: increased diffusion, allowing for the use of smaller particles, thereby increasing the external surface area and hence the reaction rate; and increased permeation into the reactive layer.

The low pressure drop and high efficiency of the particle and fiber construction allows the filter to be constructed with airflow through the face of the filter media in an axial configuration. The flexibility and thin profile of the activated carbon and fiber matrix-based filter allow the ostomy product to conform more closely to the patient's body. The filter described herein comprises, in certain embodiments, at least one outer sealable liquid impermeable, gas permeable microporous film layer; plus, an inner filter layer of adsorbent particles substantially uniformly dispersed in a fine fiber web. In some embodiments, the filter further also includes a second outer porous cover layer.

In one implementation, the carbon particle loading level is between 100 and 500 $g/m^2$, in certain implementations the carbon particle loading level is between 150 and 400 $g/m^2$, while in other implementations the carbon particle loading level is between 200 and 300 $g/m^2$. Typically, the carbon particle loading is at least 50 $g/m^2$, commonly more than 100 $g/m^2$, and optionally more than 200 $g/m^2$.

The adsorbent element 408 having adsorbent particles substantially uniformly dispersed in the fine fiber will often have a thickness of less than 5 mm, optionally less than 3 mm, and desirably less than 2 mm. In one embodiment, the adsorbent element 408 has a thickness of at least 0.01 mm. In one embodiment, the adsorbent element 408 has a thickness of not more than 10 mm. The adsorbent element 408 can have a thickness that is at least 0.25 mm. In one embodiment, the adsorbent element 408 has a thickness that is at most about 6.35 mm. In one embodiment, the adsorbent element 408 is about 1.27 ram thick.

Second Layer

In various embodiments, the filter assembly 200 can include a second layer 204. In various embodiments, the second layer 204 is configured to be liquid impermeable and gas impermeable.

The second layer 204 is preferably formed from a material that can be reliably bonded to an ostomy bag 100. Ostomy bags are typically made with materials having a low surface energy, such as ethylene vinyl acetate (EVA) plastic. A low surface energy material is defined herein as a material with a surface energy below 36 dynes/centimeters (dynes/cm). Where the second layer is also made from EVA, the materials are compatible and easily able to form a reliable bond. Alternatively, the second layer can be constructed form other compatible materials including but not limited polyethylene (PE) or polypropylene (PP).

In various embodiments, the second layer includes a material having a melt temperature at or below 120° C. In some embodiments, the melt temperature can be less than or equal to 120° C., 118° C., 115° C., 112° C., or 110° C. In some embodiments, the melt temperature can fall within a range of 90° C. to 120° C., or 95° C. to 118° C., or 100° C. to 115° C., or 105° C. to 112° C., or can be about 110° C. The melt temperature of the second layer can be determined by using a differential scanning calorimetry (DSC), using a 10-milligram sample and measurements during a second heating cycle rather than a first heating cycle.

In some embodiments of an ostomy bag, the ostomy bag walls are made of the same material as the second layer, which allows for good bonding with heat welding and similar melt temperatures. In some embodiments of an ostomy bag, the ostomy bag walls and the second layer of the filter assembly are both made of EVA.

In some embodiments of an ostomy bag, the ostomy bag walls are made of EVA and the second layer of the filter assembly is made of a material that heat bonds well with EVA. In some embodiments, the second layer of the filter assembly is made of polyethylene (PE) or polypropylene ether (PPE), which both heat bond well with EVA.

Adhesive Layer

In various embodiments, the filter assembly 200 can include an adhesive layer 410. The adhesive layer 410 is configured to seal the second layer 204 to the first layer 202. This prevents leak paths for liquid from inside the enclosure around the first layer, such as between first layer and second layer. The structure is designed to require gas to travel through the adsorbent material when exiting the closure through the filter assembly.

In some embodiments, the adhesive layer 410 can be formed from an acrylic-based pressure sensitive adhesive. A commercially available example is Acrylic Adhesive 300MP from 3M™ of St. Paul, Minnesota, USA. In some embodiments, the adhesive layer 410 can be formed from a silicone-based pressure sensitive adhesive. A commercially available example is Double Coated Tape 96042 from 3M™ of St. Paul, Minnesota, USA.

As shown in FIG. 5, the filter assembly 200 can include a distinct adhesive layer 410. In some embodiments, the adhesive layer includes a pressure sensitive adhesive. In some embodiments, the adhesive layer is a double-sided adhesive laminate. In one method, the adhesive layer 410 is bonded to second layer 204 as an early step of the filter assembly manufacturing process.

Alternatively, as shown in FIG. 6 the adhesive layer 410 can be integral with the second layer 204, such as being provided as a coating on the second layer 204. In some embodiments, the adhesive layer 410 includes a pressure sensitive adhesive. In some embodiments, the adhesive layer 410 is a double-sided adhesive laminate. In some embodiments, the adhesive layer 410 is a coating applied the second layer 204. In one method, the second layer 204 could be provided with the adhesive layer 410 already applied by its supplier, in roll form, as an input to the filter assembly manufacturing process.

Filter Assembly Openings

In various embodiments, the adhesive layer 410 can include at least a first opening 409 and the second layer 204 can include at least a second opening 411. The first opening 409 and second opening 411 are configured to at least partially overlap when the second layer 204 is bonded to the adhesive layer 410. The overlapping first opening 409 and second opening 411 from at least one filter assembly opening 306. In various embodiments, gas from an ostomy bag can exit the filter assembly 200 through the filter assembly opening.

Figure 7:
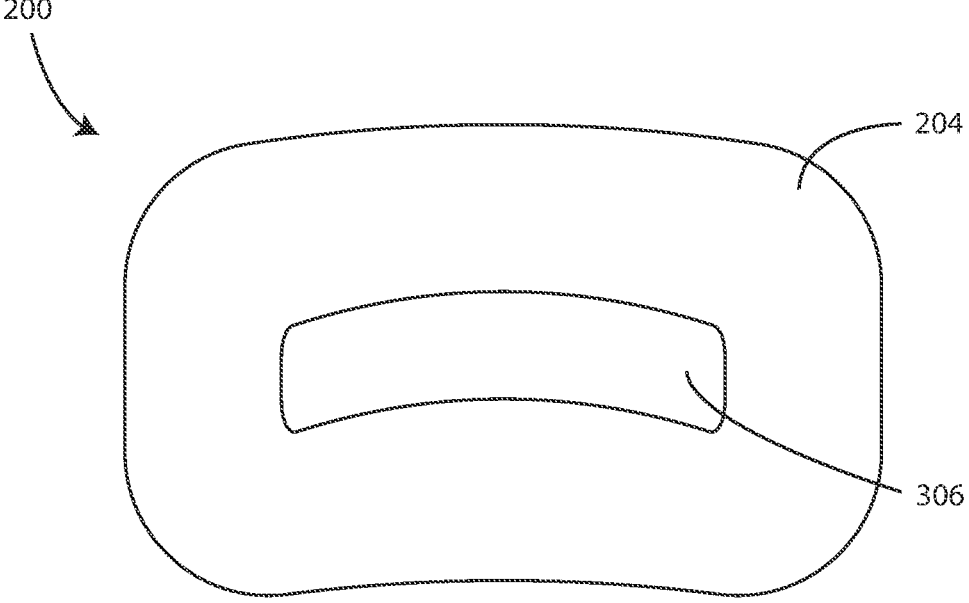
FIG. 7 is a top plan view of a first side of another embodiment of a filter assembly with a single filter assembly opening according to various embodiments herein.

In various embodiments, the filter assembly 200 can have multiple filter assembly openings 306. FIGS. 3 and 5-6 show a filter assembly 200 with two filter assembly openings 306. In an alternative embodiment, FIG. 7 shows a filter assembly 200 with a single filter assembly opening. In some embodiments, the number of filter assembly openings 306 can be greater than or equal to one, two, three, four or five 5 openings. In various embodiments the one more filter assembly opening 306 can be substantially rectangular in area. In various embodiments, the curvature of the one or more filter assembly openings 306 can match the curvature of the filter assembly. In an embodiment, the one or more filter assembly openings can be substantially rectangular in area with a set of opposing curved sides. Other sizes, shapes, and configurations of openings are imaginable to those skilled in the art.

Figure 9:
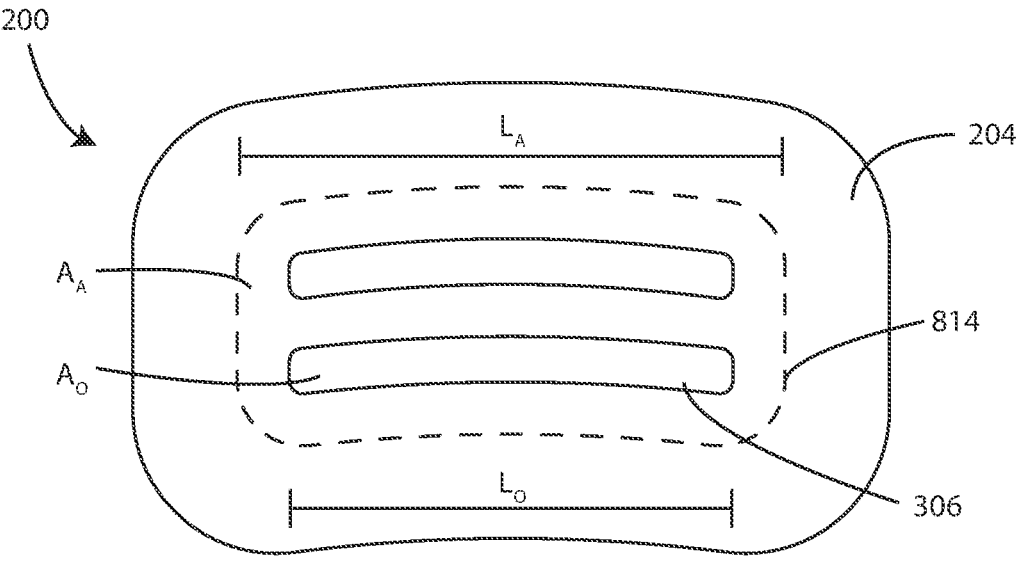
FIG. 9 is a bottom plan view of a second side of the filter assembly of FIG. 2, with broken lines showing components within the filter assembly according to various embodiments herein.

The filter assembly openings 306 are sized to allow sufficient venting of gas from an ostomy bag 100. Referring now to FIG. 9, a bottom plan view of a second side of the filter assembly of FIG. 2, with broken lines showing components within the filter assembly is shown according to various embodiments herein. The adsorbent element outer perimeter 814 is shown relative to the second layer 204. The adsorbent element 408 has a length $L_A$ and the one or more filter assembly openings 306 have a combined area $A_O$ that overlaps at least 25% of the area of one side of the adsorbent element $A_A$. In some embodiments, the length of the one or more filter assembly openings $L_O$ can overlap with greater than or equal to 50%, 55%, 60%, 65%, 70%, 75%, 80%, 85%, or 90% of the length of the adsorbent element $L_A$ or can be an amount falling within a range between any of the foregoing.

In various embodiments, the one or more filter assembly openings 306 can have a combined opening area $A_O$ that overlaps at least 25% of the area of one side of the adsorbent element $A_A$. In some embodiments, the combined opening area $A_O$ can overlap with greater than or equal to 15%, 20%, 25%, 30%, 35%, or 40% of the area of one side of the adsorbent element $A_A$ or can be an amount falling within a range between any of the foregoing.

Filter Assembly Weld Area

The weld area of the filter assembly defines where the second layer will be connected to the ostomy bag wall by a welding process. In a top or bottom plan view of the filter assembly, the weld area does not overlap with the adsorbent material. In some examples, the weld area is the extent of the second layer that is not co-extensive with the adsorbent material. The weld area has an annular shape, including an outer perimeter and an inner perimeter defining and surrounding a non-weld area. The adsorbent element is positioned with the area of the second layer that corresponds to the non-weld area. The inner perimeter of the weld area can be spaced away from an outer perimeter of the adsorbent material.

Figure 8:
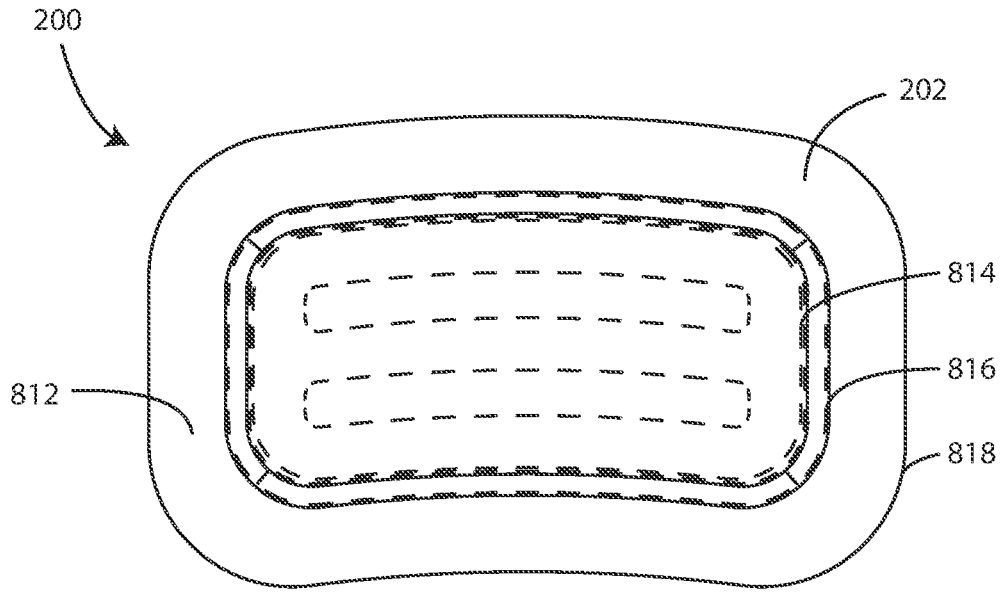
FIG. 8 is a top plan view of a first side of the filter assembly of FIG. 2, with broken lines showing components within the filter assembly according to various embodiments herein.

Referring now to FIG. 8, a top plan view of a first side of the filter assembly of FIG. 2 is shown, with broken lines illustrating components within the filter assembly, according to various embodiments herein. In various embodiments, the filter assembly 200 can have a weld area 812 where an annular welding tool can contact the first layer 202 of the filter assembly and weld the second layer 204 of the filter assembly to an ostomy bag 100. The filter assembly 200 can have an outer perimeter 818 defining the outer edge of filter assembly and an inner perimeter 816 defining where the first layer 202 contacts the adhesive layer 410 and the second layer 204. In various embodiments the weld area 812 is an annular area disposed between the inner perimeter 816 and the outer perimeter 818. In some embodiments, the weld area extends substantially the entire distance between the inner perimeter 816 and the outer perimeter 818. Alternatively, the weld area 812 can span a fraction of the distance between the inner perimeter 816 and the outer perimeter 818, such as at least or about 50%, 75%, 80%, 85%, 90%, 95%, or 98%. As shown in FIG. 8, The adsorbent element outer perimeter 814 is disposed inside of the filter assembly inner perimeter 816. The area inside of the inner perimeter 816 can form a non-weld area. In some embodiments, the inner perimeter 816 is spaced away from the adsorbent element outer perimeter 814 by a first margin distance. The inner perimeter of the weld area could the as the filter assembly inner perimeter 816, in some examples. In other examples, the inner perimeter of the weld area could be spaced away from the adsorbent element outer perimeter 814 by a second margin distance that is larger than the first margin distance.

In various embodiments, the second layer of the filter assembly does not include any adhesive on a first side that is connected to the carrier layer and which will be bonded to the ostomy bag. In these embodiments, the carrier layer may still include adhesive which removably secures the second layer of the filter assembly to the carrier layer. However, the bag side of the filter assembly, is free of adhesive in various embodiments.

Flow of Gas Though the Filter Assembly

Ostomy bag filters may be of the axial flow type, or more commonly the so-called radial flow type or lateral flow type. These and other flow path types are described in commonly owned U.S. Pat. No. 8,979,811, issued on Mar. 17, 2015, which is incorporated herein by reference in its entirely. For ostomy bag applications, a filter of the radial or lateral flow type is most common because it allows for the construction of a low-profile filter that also provides an extended flow path for deodorizing the flatus gases. Radial flow type and lateral flow type filters have larger adsorbent path lengths, resulting in increased adsorbent properties. However, a larger adsorbent path length is expected to decrease the air flow through the filter. Conversely, axial flow type filters are expected to have higher levels of air flow due to a shorter adsorbent path length.

Figure 10:
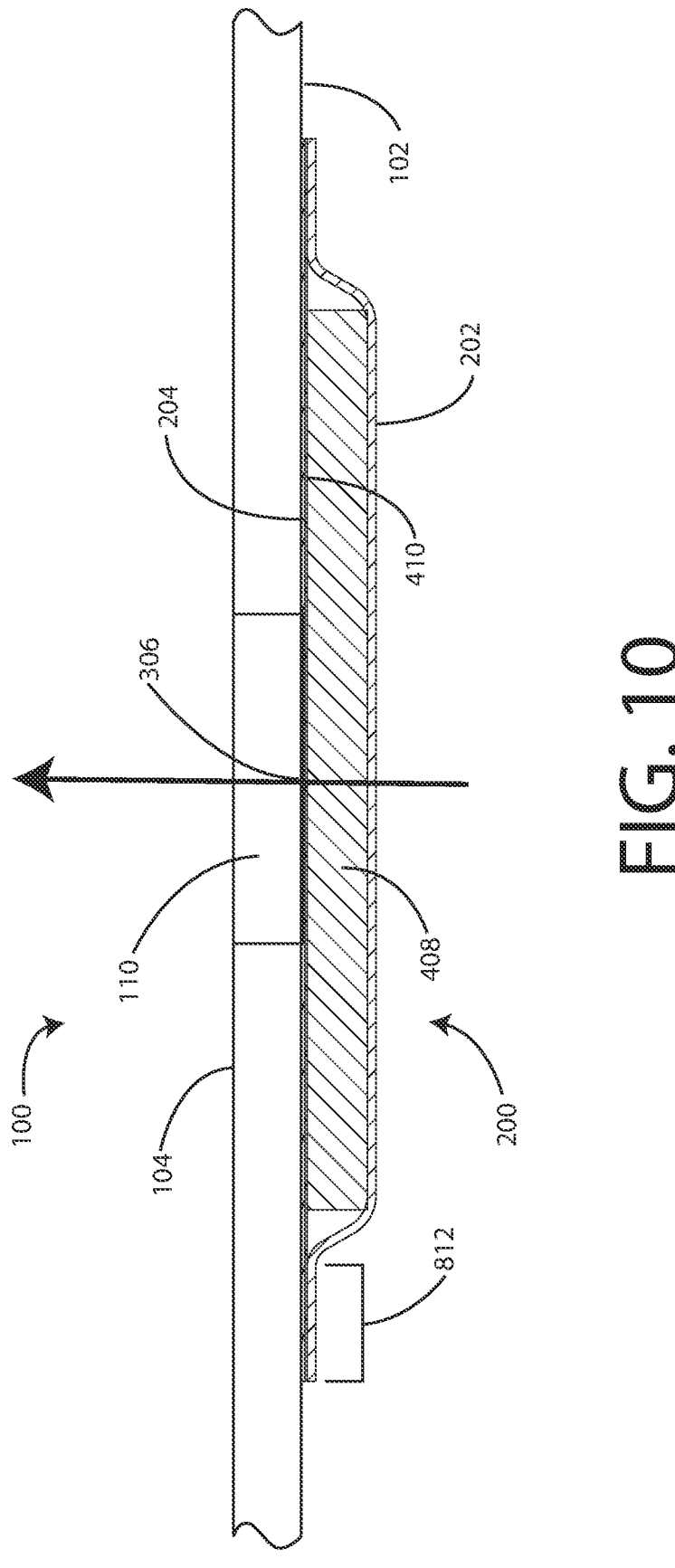
FIG. 10 is a cross-sectional view of the filter assembly of FIG. 2 welded to an ostomy bag, where the filter assembly has an axial flow path through the filter assembly according to various embodiments herein.

FIG. 10 is a cross-sectional view of the filter assembly of FIG. 2 welded to an ostomy bag, where the filter assembly has an axial flow path through the filter assembly, according to various embodiments herein. In various embodiments, the filter assembly 200 can include a first layer 202, an adhesive layer 410, an adsorbent element 408, and a second layer 204. The filter assembly 200 can be welded to the ostomy bag 100 such that the second layer 204 of the filter assembly is bonded to the interior surface 102 of ostomy bag along annular weld area 812. The filter assembly 200 is positioned to be aligned with a vent opening 110 of the ostomy bag 100. In various embodiments, gas from the ostomy bag enters the filter assembly 200 though the first layer 202 and exits the filter assembly through the filter assembly opening 306. The arrow in FIG. 10 denotes an exemplary gas flow path in which gas flows axially though the filter assembly 200. In an embodiment, gas from the ostomy bag 100 enters the filter assembly 200 though the first layer, flows axially through the adsorbent layer, and exits the filter assembly through the filter assembly opening 306.

Figure 11:
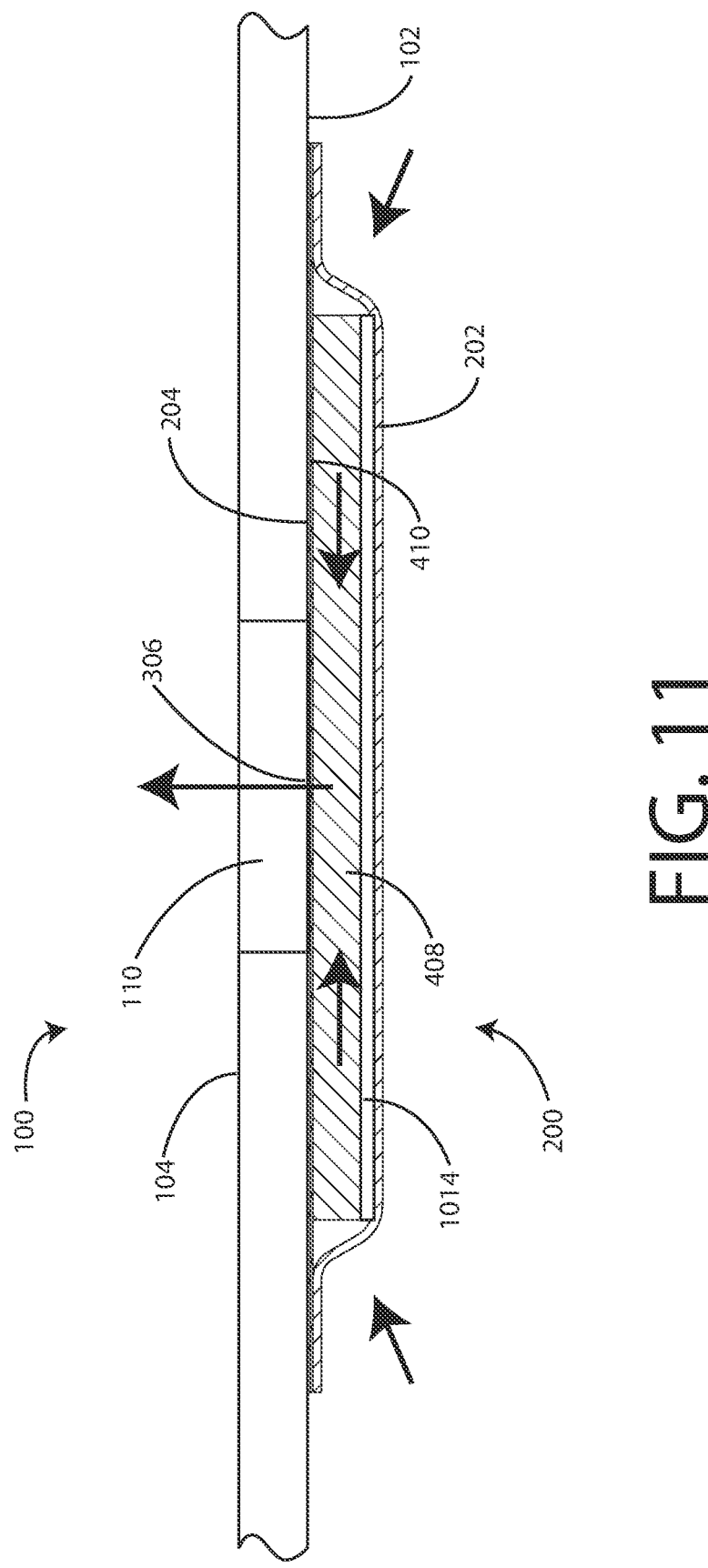
FIG. 11 is a cross-sectional view of yet another embodiment of a filter assembly welded to an ostomy bag, wherein the filter assembly has a lateral flow path through the filter assembly according to various embodiments herein.

Referring now to FIG. 11, a cross-sectional view of yet another embodiment of a filter assembly is shown welded to an ostomy bag, wherein the filter assembly has a lateral flow path through the filter assembly, according to various embodiments herein. In various embodiments, the filter assembly 200 can include a first layer 202, an adhesive layer 410, an adsorbent element 408, and a second layer 204. The filter assembly 200 can be welded to the ostomy bag 100 such that the second layer 204 of the filter assembly is bonded to the interior surface 102 of ostomy bag along an annular weld area 812. Filter assembly 200 is positioned to be aligned with a vent opening 110 of the ostomy bag 100. As shown in FIG. 11, the filter assembly can include a barrier layer 1014 disposed between the first layer 202 and the adsorbent element 408. The barrier layer 1014 is configured to obstruct the flow of gas through the filter assembly from the direction of a first side of the adsorbent element 408. The barrier layer 1014 is configured to be gas impermeable such that gas from the ostomy bag can only enter the adsorbent element 408 where the barrier layer is not present. The arrows in FIG. 11 denotes an exemplary gas flow path in which gas flows laterally though the filter assembly 200. In various embodiments, gas from the ostomy bag 100 enters the filter assembly 200 though the gas permeable first layer, enters the adsorbent element 408 through the sides where barrier layer 1014 is not present, flows laterally through the adsorbent element 408, and exits the filter assembly through the filter assembly opening 306.

Method of Producing an Array of Filter Assemblies

Referring now to FIG. 12, a method of manufacturing filter assemblies is shown according to various embodiments herein. The method 1300 at step 1302 can include providing a first layer sheet 1202, an adhesive layer 1208, an adsorbent layer sheet, a second layer sheet 1204, and a carrier sheet 1210. The sheets provided in this method can be used to produce one or more filter assemblies 200. In various embodiments, the first layer sheet is configured to be gas permeable and liquid impermeable, the adsorbent layer comprises a gas-adsorbing material, the second layer comprises a material having a melt temperature at or below 120° C., and the carrier layer comprises a carrier adhesive disposed on an adhesive side of the carrier. In some embodiments, the second layer sheet 1204 and the adhesive layer 1208 are provided separately. In some embodiments, the second layer sheet 1204 and the adhesive layer 1208 are provided as a single sheet, such that the second layer sheet is bonded to the adhesive layer.

The method 1300 at step 1304 can include bonding the second layer sheet 1204 to the adhesive layer 1208 to form a second layer subassembly 1400 having a first side 1205 and an opposite adhesive layer side 1209. The term subassembly is used to refer to the output of a step in a production process for either a single filter assembly or an array of multiple filter assemblies. In some embodiments, the adhesive layer 1208 comprises a pressure sensitive adhesive and the second layer subassembly 1400 is formed by compressing the second layer sheet 1204 and the adhesive layer 1208. Various means of bonding the second layer sheet 1204 to the adhesive layer 1208 are imaginable to those skilled in the art, including pressure bonding, heat bonding and the like. In an alternative embodiment, the second layer sheet 1204 and the adhesive layer 1208 are supplied to the process prebonded such that the second layer subassembly 1400 is already formed and this step can be omitted. In various embodiments, the second layer subassembly 1400 is formed at least 24 hours before forming the plurality of filter assembly perimeters in step 1316. In some embodiments, the second layer subassembly 1400 is formed greater than or equal to 1, 4, or 7 days, or an amount falling within a range between any of the foregoing, before forming the plurality of filter assembly perimeters in step 1316.

Pre-bonding the second layer sheet 1204 to the adhesive layer 1208 increases the dwell time between those two layers. In the context of this method, dwell time is defined as the length of time that one material is in contact another. In various embodiments, longer dwell times increase the strength of the bond between the second layer sheet 1204 to the adhesive layer 1208. In some embodiments, the dwell time can be greater than or equal to 1, 4, or 7 days, or can be at least 1, 2, 3 or 4 days, or can be an amount falling within a range between any of the foregoing. In some embodiments, the dwell time can be less than or equal to 24, 20, 16, 12, 8, 4, or 1 hour, or can be an amount falling within a range between any of the foregoing.

In some embodiments, pressure is applied to the second layer subassembly 1400 during the dwell time. In an embodiment, pressure is applied by winding the second layer subassembly 1400 into a supply roll. Other means of applying pressure are possible, including applying a roller, weighted object, or the like to the second layer subassembly 1400. In some embodiments, the pressure applied to the second layer subassembly 1400 can be greater than or equal to 1 kilopascal (kPa), 11 kPa, 21 kPa, 30 kPa, 40 kPa, or 50 kPa. In some embodiments, the pressure applied to the second layer subassembly 1400 can be less than or equal to 100 kPa, 90 kPa, 80 kPa, 70 kPa, 60 kPa, or 50 kPa. In some embodiments, the pressure can fall within a range of 1 kPa to 100 kPa, or 11 kPa to 90 kPa, or 21 kPa to 80 kPa, or 30 kPa to 70 kPa, or 40 kPa to 60 kPa, or can be about 50 kPa. In some embodiments, pressure can be applied to the second layer subassembly 1400 for greater than or equal to 1, 4, or 7 days, or at least 1, 2, 3 or 4 days, or for an amount falling within a range between any of the foregoing. In some embodiments, pressure can be applied to the second layer subassembly 1400 for less than or equal to 24, 20, 16 hours, 12, 8, 4, or 1 hour, or can be an amount falling within a range between any of the foregoing.

The method 1300 at step 1306 can include cutting through the second layer subassembly 1400 to define a plurality of filter assembly openings 306 in the second layer subassembly. In various embodiments, the filter assembly openings 306 are cut with a knife, but other means of cutting are imaginable to those skilled in the art, including die cutting, laser cutting and the like. Various numbers, shapes, and configurations of filter assembly openings 306 can be cut into the second layer subassembly. The filter assembly openings 306 can be cut in sets comprising 1, 2, or more openings. Each set of filter assembly openings 306 can accommodate one filter assembly 200. In various embodiments, the sets of filter assembly openings 306 are spaced sufficiently far apart to accommodate the outer perimeter 818 of a filter assembly. In some embodiments, the waste material produced by cutting the filter assembly openings 306 is subsequently removed from the second layer subassembly 1400. A vacuum device, picker device, human operator, or part of the cutting equipment can be used to remove the waste material or other techniques can be used.

Figure 13:
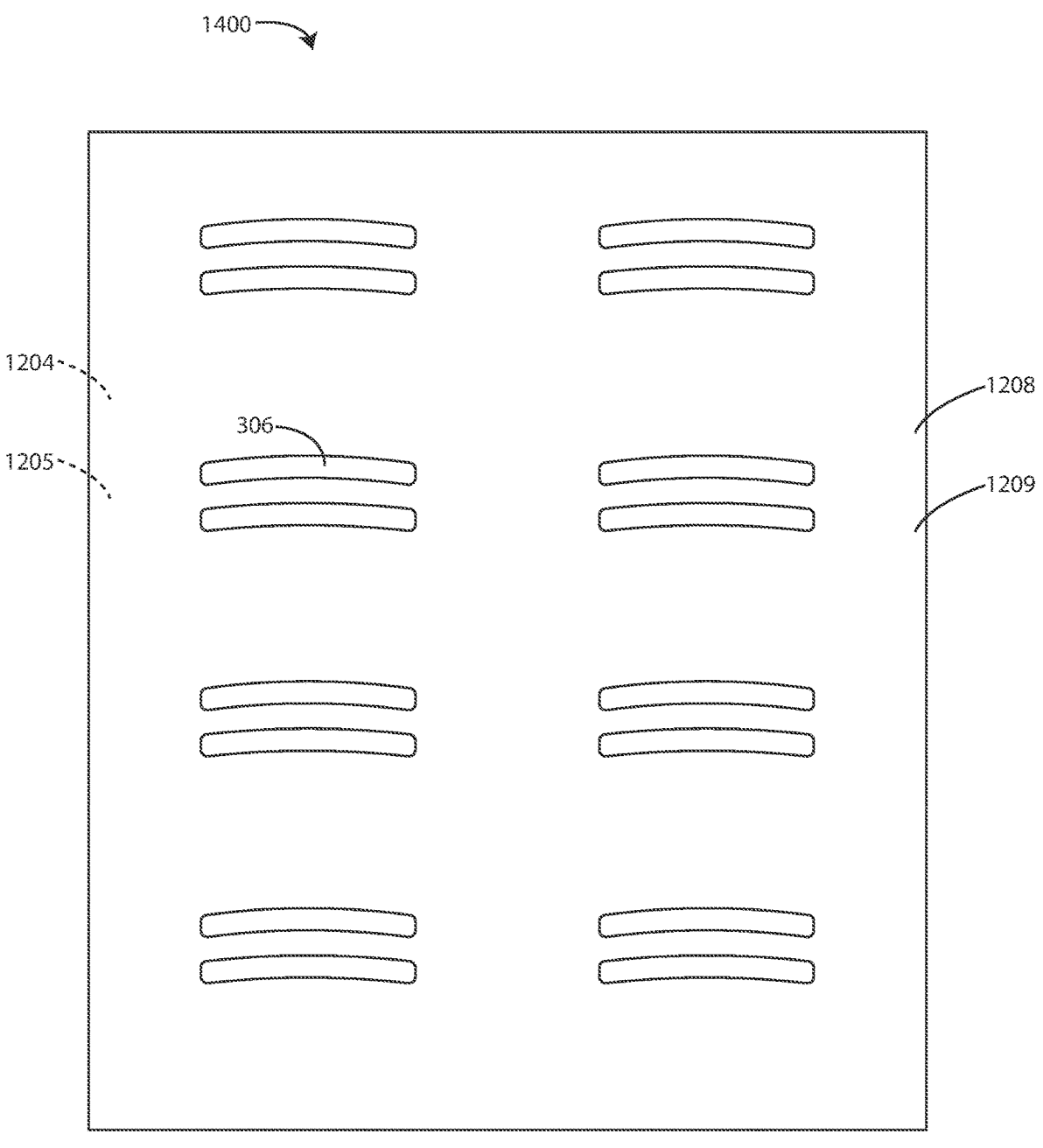
FIG. 13 is a top view of a second layer subassembly according to various embodiments herein.

Referring now to FIG. 13, a top view of a second layer subassembly 1400 is shown according to various embodiments herein. The second layer subassembly 1400 can include a second layer sheet 1204 and an adhesive layer 1208 bonded together. The second layer subassembly 1400 can include a first side 1205 (not visible in this view) and an adhesive layer side 1209. In various embodiments, the first side 1205 of the second layer subassembly 1400 is formed by the second layer sheet 1204. In various embodiments, the adhesive layer side 1209 of the second layer subassembly is formed by the adhesive layer 1208. In various embodiments, a plurality of filter assembly openings 306 are cut in the second layer subassembly 1400.

The method 1300 at step 1308 can include removably attaching the first side 1205 of the second layer subassembly 1400 to the adhesive side of the carrier sheet 1210 to form a first carrier subassembly 1450 having a first side and an opposite adhesive layer side. In various embodiments, the carrier sheet 1210 includes a low tack adhesive or static cling material to removably attach the second layer subassembly 1400 to the carrier sheet. In the context of this application, a low tack adhesive is defined as an adhesive that can attach an object (such as a filter assembly or the like) to an adhesive carrier, so that the object will adhere to the adhesive carrier when pressure is applied, the object will be held in place as the adhesive carrier is moved, and the object can be removed from the adhesive carrier without damaging the object or leaving substantial amounts of adhesive on the object's surface. In some embodiments, the adhesive side of the carrier sheet 1210 includes a pressure sensitive adhesive and the first carrier subassembly 1450 is formed by compressing second layer subassembly 1400 to the adhesive side of the carrier sheet 1210.

The method 1300 at step 1310 can include cutting the adsorbent layer sheet into a plurality of adsorbent elements 408. In various embodiments, the adsorbent elements 408 are cut from adsorbent layer sheet with a knife, but other means of cutting are imaginable to those skilled in the art, including die cutting, laser cutting and the like. In various embodiments, the adsorbent elements can be cut prior to or during steps 1304, 1306 or 1308.

The method 1300 at step 1312 can include placing the plurality of adsorbent elements 408 on the adhesive layer side of the first carrier subassembly 1450 such that each of the plurality of filter assembly openings is covered by one of the plurality of adsorbent elements, thereby forming a second carrier subassembly 1500 having a first side 1205 and an adhesive layer side 1209. In various embodiments an adsorbent element 408 is placed over each set of openings cut in step 1306. In some embodiments, each adsorbent element 408 covers a single filter assembly opening 306. In other embodiments, each adsorbent element covers two, three, or more filter assembly openings 306 that make up a set of filter assembly openings. In various embodiments, the adhesive layer 1208 holds the adsorbent elements 408 in place on the second carrier subassembly 1500.

Figure 14:
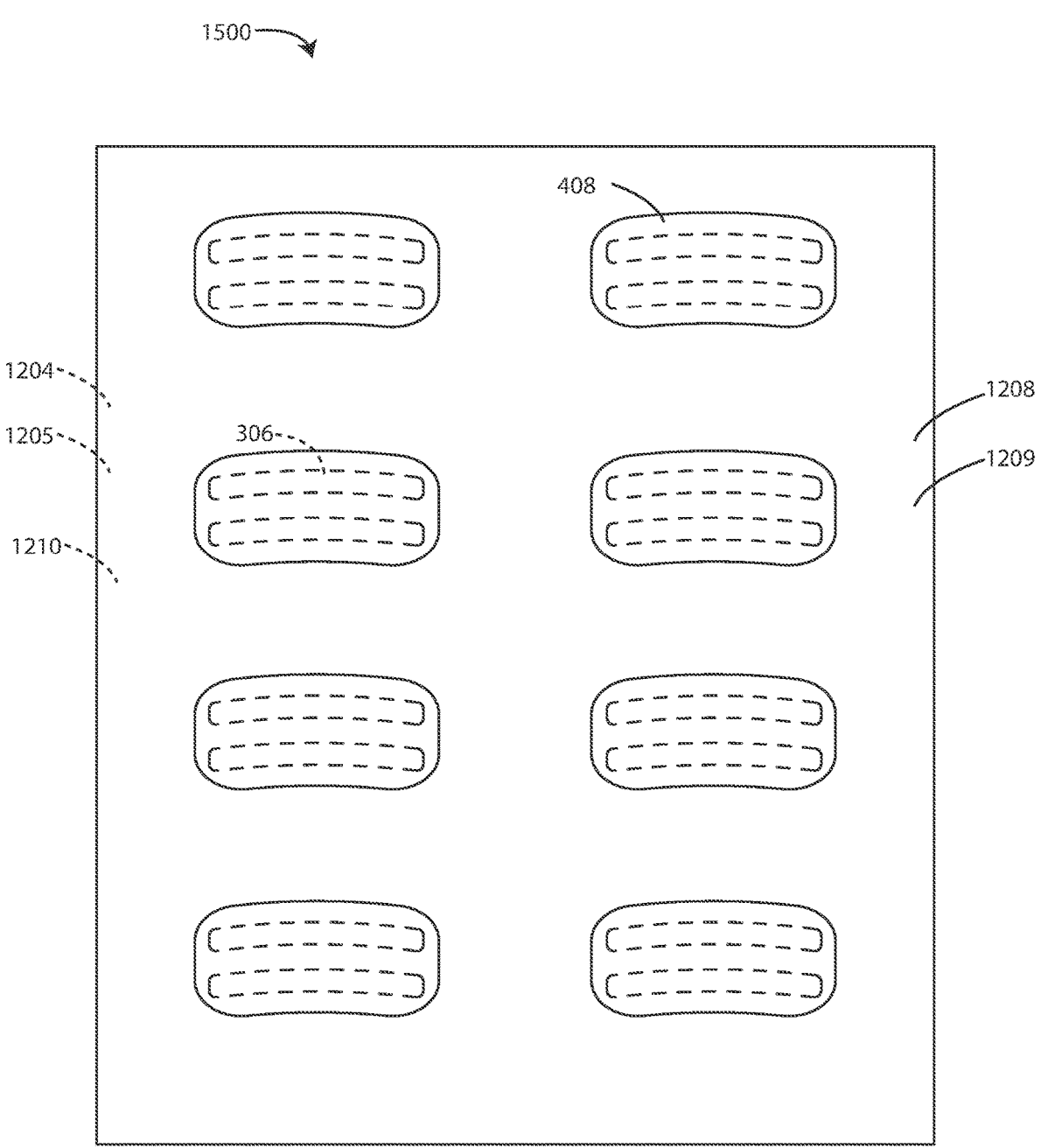
FIG. 14 is a top view of a second carrier subassembly according to various embodiments herein.

Referring now to FIG. 14, a top view of a second carrier subassembly 1500 is shown according to various embodiments herein. The second carrier subassembly 1500 can include a first side 1205 and an adhesive layer side 1209. In various embodiments, the first side 1205 of second carrier subassembly 1500 is formed from carrier sheet 1210 and the adhesive layer side 1209 of the second carrier subassembly is formed from the adhesive layer 1208. The second carrier subassembly 1500 is formed by placing the plurality of adsorbent elements 408 on the adhesive layer side 1209 of the first carrier subassembly 1450 such that each set of filter assembly openings 306 is covered by one of the plurality of adsorbent elements 408. As shown in FIG. 14, the adsorbent elements are placed on the second carrier subassembly 1500 such that each adsorbent element 408 is substantially centered with each set of filter assembly openings 306.

In some embodiments, the carrier sheet 1210 is joined to the second layer subassembly 1400 before the filter openings are cut. In other embodiments, the carrier sheet 1210 is joined to the second layer subassembly 1400 after the filter openings are cut, as illustrated in the flowchart of FIG. 12.

The method 1300 at step 1314 can include bonding the first layer to the adhesive layer side 1209 of the second carrier subassembly 1500 such that the adsorbent elements 408 are disposed between the first and second layers to form an uncut filter assembly 1600. In some embodiments, the adhesive layer 1208 comprises a pressure sensitive adhesive and the uncut filter assembly 1600 is formed by compressing the first layer sheet 1202 and the adhesive layer 1208. The first layer sheet 1202 and the adhesive layer 1208 can be compressed by a roller, a weighted object, or the like.

The method 1300 at step 1316 can include forming a plurality of filter assembly perimeters 818 around each of the adsorbent elements 408 by simultaneously cutting through the first layer sheet 1202, adhesive layer 1208, and second layer sheet 1204, but not through the carrier sheet 1210, resulting in a plurality of filter elements 200 disposed on the carrier sheet 1210. In various embodiments, the first layer, second layer and the adhesive layer have substantially aligned outer perimeters such that each filter assembly perimeter 818 can be formed in a single cut. In some embodiments, the number of filter assembly perimeters cut into the uncut filter assembly 1600 can be greater than or equal to 1, 10, 20, 30, 40, or 50 perimeters, or can be an amount falling within a range between any of the foregoing.

Figure 15:
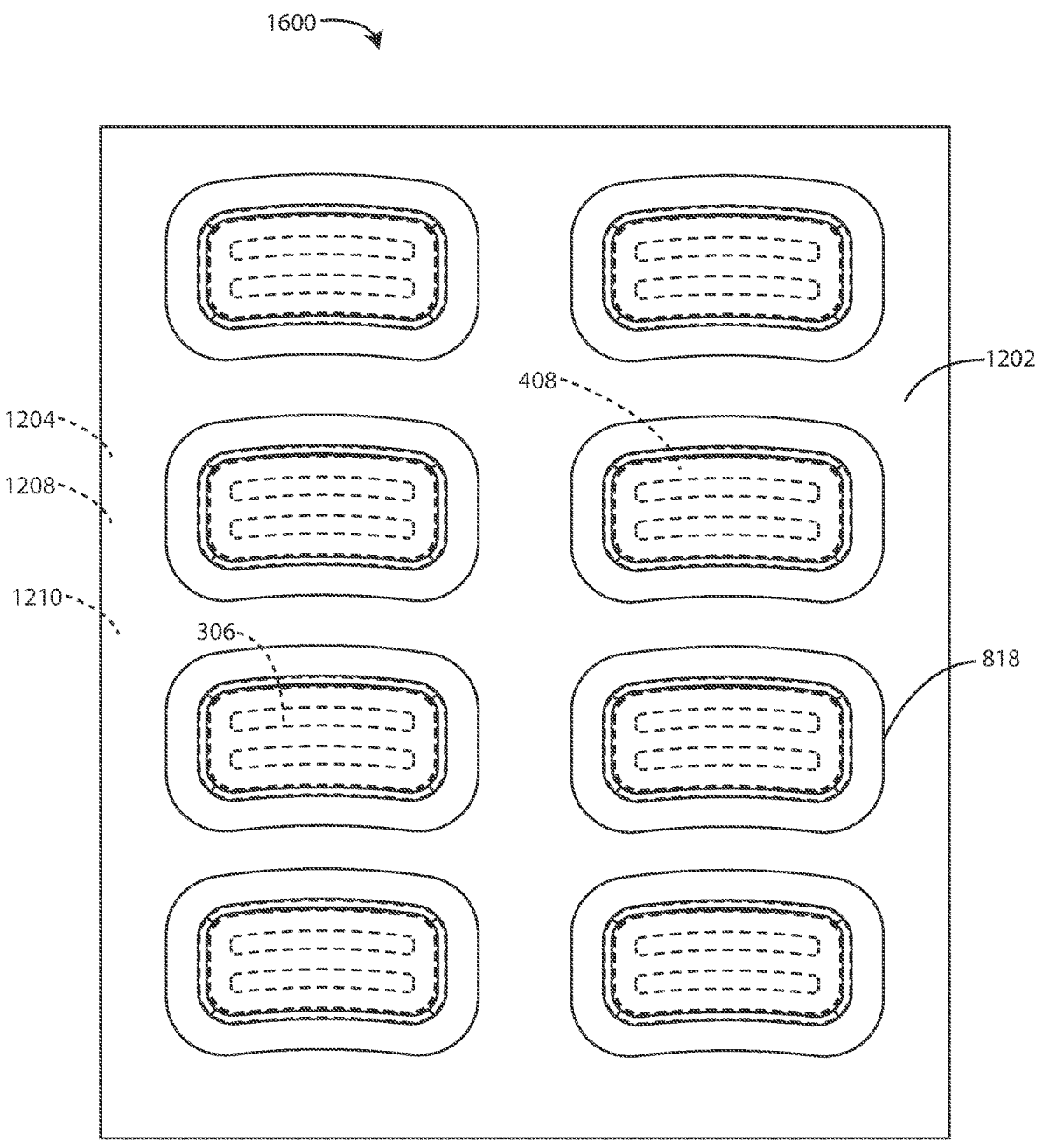
FIG. 15 is a top view of an uncut filter assembly according to various embodiments herein.

Referring now to FIG. 15, a top view of an uncut filter assembly 1600 is shown according to various embodiments herein. In various embodiments the uncut filter assembly 1600 comprises a first layer sheet 1202, second layer sheet 1204, adhesive layer, 1208, carrier sheet, and one or more adsorbent elements 408 bonded together.

The method can further include removing the waste matrix after cutting the filter assembly perimeters 818 in step 1316. In various embodiments, the waste matrix comprises excess material from the first layer sheet 1202, second layer sheet, 1204, and adhesive layer 1208. A vacuum device, picker device, human operator, or part of the cutting equipment can be used to remove the waste material or other techniques can be used.

Figure 16:
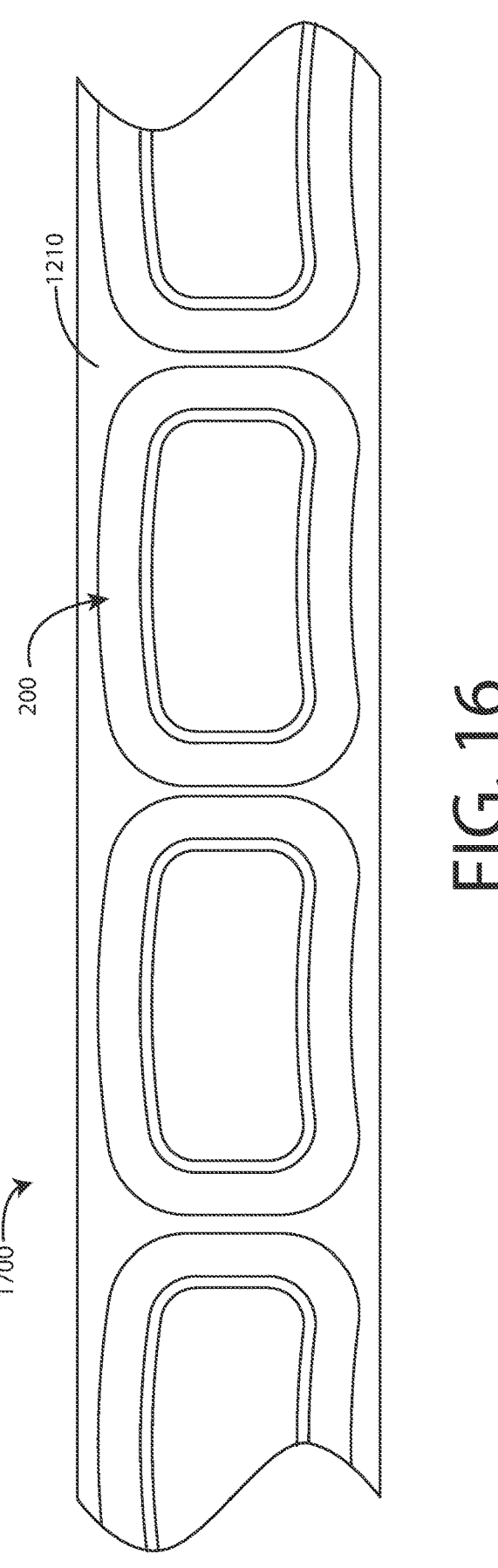
FIG. 16 top view of an array of filter assemblies on a release liner according to various embodiments herein.

After the waste matrix is removed, an array of filter assemblies 200 removably attached to a carrier 1210 remain Such an array can be seen in FIG. 16. By removably attached to a carrier, it is meant that the filter assemblies can be easily removed from the carrier 1210 without damaging the carrier 1210 or the filter assembly.

In various embodiments, the method comprises forming the plurality of filter assembly perimeters at least 24 hours before applying a filter assembly 200 of the filter assembly array 1700 to an ostomy bag 100. In some embodiments, the method comprises forming a filter assembly on a carrier 1210 at least greater than or equal to 1 day, 4 days, or 7 days, or by an amount falling within a range between any of the foregoing, before applying the filter assembly 200 to an ostomy bag 100.

In some embodiments, allowing the filter assembly array to remain intact increases the dwell time between the layers. In the context of this method, dwell time is defined as the length of time that one material is in contact another. In various embodiments, longer dwell times increase the strength of the bond between the first layer 202, second layer, 204, adhesive layer 410, and adsorbent element 408 of each filter assembly 200. In some embodiments, the dwell time can be greater than or equal to 1 days, 4 days, or 7 days, or can be an amount falling within a range between any of the foregoing. In some embodiments, the dwell time can be less than or equal to 24 hours, 20 hours, 16 hours, 12 hours, 8 hours, 4 hours, or 1 hours, or can be an amount falling within a range between any of the foregoing.

Referring now to FIG. 16, a top view of a filter assembly array 1700 is shown according to various embodiments herein. The filter assembly array 1700 includes one or more filter assemblies 200 removably attached to a carrier sheet 1210. The carrier sheet 1210 can include a low-tack adhesive or static cling material to hold the filter assemblies 200 onto the carrier layer sheet. The filter assembly array of FIG. 16 includes one filter assembly 200 per row. However, filter assembly arrays 1700 with two or more filter assemblies 200 per row are possible.

In some embodiments, pressure is applied to the filter assembly array 1700 during the dwell time. In an embodiment, pressure applied by winding the filter assembly array 1700 into a filter element supply roll 1220. Other means of applying pressure are possible, including applying a roller, weighted object, or the like to the filter assembly array 1700. In some embodiments, the pressure applied to the second layer subassembly 1400 can be greater than or equal to 1 kPa, 11 kPa, 21 kPa, 30 kPa, 40 kPa, or 50 kPa. In some embodiments, the pressure applied to the second layer subassembly 1400 can be less than or equal to 100 kPa, 90 kPa, 80 kPa, 70 kPa, 60 kPa, or 50 kPa. In some embodiments, the pressure can fall within a range of 1 kPa to 100 kPa, or 11 kPa to 90 kPa, or 21 kPa to 80 kPa, or 30 kPa to 70 kPa, or 40 kPa to 60 kPa, or can be about 50 kPa. In some embodiments, pressure can be applied to the second layer subassembly 1400 for greater than or equal to 1 days, 4 days, or 7 days, or can be an amount falling within a range between any of the foregoing. In some embodiments, pressure can be applied to the second layer subassembly 1400 for less than or equal to 24 hours, 20 hours, 16 hours, 12 hours, 8 hours, 4 hours, or 1 hours, or can be applied for a duration falling within a range between any of the foregoing.

Figure 17:
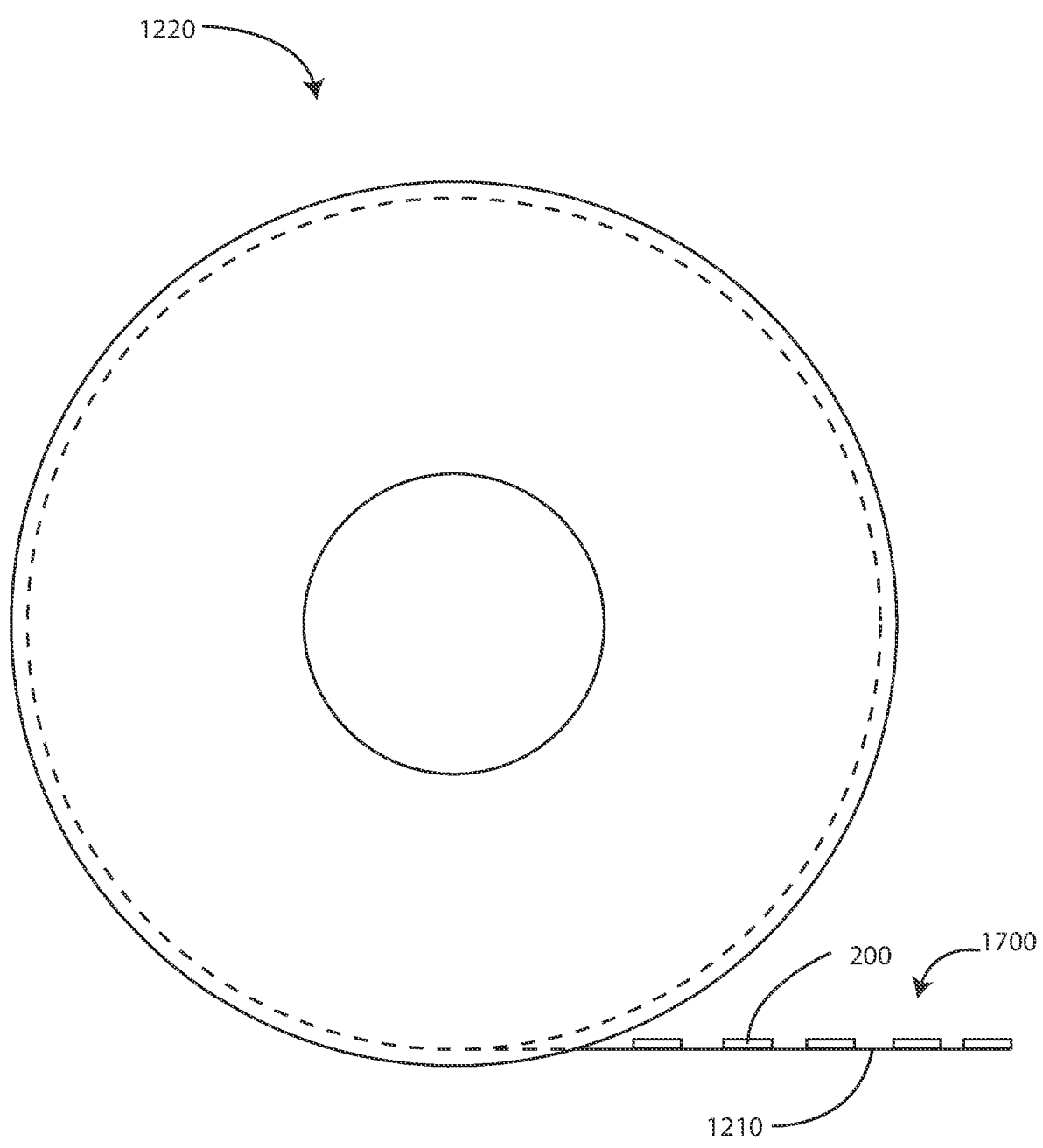
FIG. 17 is a side view of a roll of filter assemblies on a release liner according to various embodiments herein.

Referring now to FIG. 17, a side view of a roll of a filter array is shown according to various embodiments herein. The method can further include winding the plurality of filter elements disposed on the carrier layer into a filter element supply roll 1220. In various embodiments, the adhesive layer 410 of each filter assembly 200 comprises a pressure sensitive adhesive and winding of the plurality of filter assemblies 200 disposed on the carrier sheet 1210 into the filter element supply roll 1220 compresses the first layer 202, adhesive layer 410, and second layer 204.

The filter assemblies can then be bonded to ostomy bags.
Method of Bonding a Filter Assembly to an Ostomy Bag Referring now to FIG. 1, a top view of an ostomy bag having a filter assembly is shown according to various embodiments herein. The ostomy bag 100 includes a stoma opening 106 into an interior surface 102 of the ostomy bag. The stoma opening 106 is surrounded by a flange 108, which is where the ostomy bag will be connected to the user's stoma. The ostomy bag 100 also defines a vent opening 110.

The filter assembly 200 has a second layer 204 configured to be bonded to the ostomy bag 100 and first layer 202 opposite from the second layer. The filter assembly 200 also includes a weld area 812 surrounding the adsorbent element 408 and filter assembly opening 306, where the filter assembly is weldable to the ostomy bag 100.

The filter assembly 200 is removed from the carrier sheet 1210 to reveal the second layer 204 of the filter assembly. The filter assembly 200 is then placed on a surface of the ostomy bag 100 over the vent opening 110, so that the second layer 204 of the filter assembly contacts the bag surrounding the vent opening. The removal of the filter assembly and the placement of the filter assembly on the ostomy bag can be done manually by a person or in an automated way using a machine.

After placing the filter assembly 200 on the ostomy bag 100, a permanent seal is formed between the filter assembly and the ostomy bag. The permanent seal may be formed by heat sealing, radiofrequency welding, or ultrasonic welding. The permanent seal may be formed using an annular shaped welding tool. The permanent seal prevents gaseous or liquid by-pass of the filter assembly 200. The seal is accomplished by applying energy to the filter assembly 200, especially the second layer 204, at the weld area 812, so that it creates a bond to the material of the ostomy bag 100. The weld area can be annular and includes an inner perimeter defining an open area containing the footprint of the adsorbent element 408. In various embodiments, the manufacturing process does not apply heat or other energy to the adsorbent element 408. In these embodiments, the weld tool is therefore configured to apply energy in an annular pattern and to not apply energy to the adsorbent element 408. The welding tool can be brought into contact with the filter assembly manually by a person or in an automated way using a machine.

In one embodiment, second layer 204 of the filter assembly 200 is adhered to an interior surface 102 of the ostomy bag 100 over the vent opening 110. In another embodiment, the second layer 204 of the filter assembly 200 is adhered to an exterior surface 104 of the ostomy bag 100 over the vent opening 110.

The embodiments described allow for a convenient and efficient assembly method with a highly reliable seal between the ostomy bag 100 and the filter assembly 200. One of the most convenient ways of connecting filter assembly 200 to an ostomy bag 100 would be to use only a pressure-sensitive adhesive to create the seal between the ostomy bag and the filter assembly. With only pressure-sensitive adhesive and no heat seal, there is no need for the equipment that is used to create the seal. The workers assembling the bags would simply expose the adhesive and place the filter over the vent opening. In contrast, the use of a heat-sealing process requires preparation of the heat-sealing equipment, the careful placement of the filter over the vent opening and maintaining the typically small and lightweight filter in that position while the heat-sealing equipment is precisely applied. However, ostomy bags are typically made with materials having a low surface energy, such as ethylene vinyl acetate (EVA) plastic, because the low surface energy of the material makes it easy to completely empty the bag when necessary. But the low surface energy of the bag material causes concern that the pressure-sensitive adhesive seal will not be reliable. Any leakage at the filter assembly would be unacceptable. A low surface energy material is defined herein as a material with a surface energy below 36 dynes/cm.

As a result, heat sealing of the filter assembly to the ostomy bag is a preferred method over using adhesive for connecting filter assemblies to ostomy bags. There are concerns with reliability of adhesive-only seals using pressure-sensitive adhesive.

Additional options for materials and manufacturing methods are described in commonly owned U.S. Pat. No. 8,979,811, issued on Mar. 17, 2015, which is incorporated herein by reference in its entirely.

Method of Producing at least one Filter Assembly

Methods of manufacturing an array of filter assemblies have been described in detail above. Methods of producing one or more filter assemblies are also contemplated. Aspects of system/device operation described elsewhere herein can be performed as operations of one or more methods according to various embodiments herein.

In an embodiment, a method of manufacturing a filter assembly is included. The method can include providing sheets of a first layer, an adhesive layer, an adsorbent element, a second layer, and a carrier layer. In some embodiments, the first layer is configured to be gas permeable and liquid impermeable, the adsorbent element includes a gas-adsorbing material, the second layer includes a material having a melt temperature at or below 120° C., and the carrier layer includes a carrier adhesive disposed on an adhesive side of the carrier. The method can include bonding the second layer to the adhesive layer. The method can include simultaneously cutting through the second layer and adhesive layer to form an opening. The method can include removably attaching the second layer to an adhesive side of the carrier layer. The method can include cutting the adsorbent element into discrete adsorbent elements. The method can include placing one of the discrete adsorbent elements to cover the opening of the adhesive layer. The method can include bonding the first layer to the adhesive layer, such that the adsorbent element is disposed between the first and second layers. The method can include forming a perimeter around the adsorbent element by simultaneously cutting through the first layer, adhesive layer, and second layer resulting in a filter element disposed on the carrier layer resulting in a filter assembly.

Polymeric Fine Fibers

As described above, in certain implementations the adsorbent element 408 or filter media described herein utilizes a fiber matrix into which activated carbon particles or fibers are incorporated, such as, for example, electro spun polymeric fine fibers are shown. These fine fibers are also referred to as nanofibers. No additional binders or other non-active materials are generally needed to construct the activated carbon and fiber matrix. As the micrographs depict, binding the particles with fine fiber minimizes void space, resulting in a near optimal adsorption capacity per given volume while providing the tortuous path necessary for the gases to diffuse. The soft, strong, and flexible nature of the fine fiber makes the activated carbon and fiber matrix an ideal structure for use as a wearable adsorbent/absorbent.

A fiber matrix that can be used is described in Published PCT Patent Application WO2007/095363, which is hereby incorporated by reference in its entirety. The fiber has a diameter of about 0.001 to about 2 microns, 0.001 to about 1 micron, 0.001 to about 0.5 micron, or 0.001 to about 5 microns, A variety of techniques can be used for the manufacture of small diameter fine fibers. One method involves passing polymeric material through a fine capillary or opening either as a melted material or in a solution that is subsequently evaporated. Fibers can also be formed by using "spinnerets" typical for the manufacture of synthetic fiber such as nylon. Electrostatic spinning is often the method of choice for forming the fine fiber nonwoven webs of the invention. Such techniques involve the use of a hypodermic needle, nozzle, capillary or movable emitter. These structures provide liquid solutions of the polymer that are then attracted to a collection zone by a high voltage electrostatic field. As the materials are pulled from the emitter and accelerate through the electrostatic zone, the fiber becomes very thin and can be formed in a fiber structure by solvent evaporation.

Another method involves using melt blown plastic or polymeric material to generate substantially uniformly dispersed fine fiber web. In general, melt blown fibers typically useable according to the present invention are an air laid continuous extrusion of fibers joined to each other to form a sheet of layer of filter material. The adsorbent particles of the present invention can be substantially uniformly dispersed in the fine fiber web. Plastics such as polypropylene, polystyrene, and polyester may be used.

Incorporation of Adsorptive and Reactive Particles

In an example method, particles are incorporated into the fine fiber nonwovens generally by feeding the particles into a flow of polymer solution using a volumetric screw feeder with an auger. In some embodiments it is advantageous to further use a deflocculator to divide agglomerated particles. The particles are then deposited along with the polymer solution and become entangled within the fine fiber network as it forms upon drying of the polymer solution. In typical embodiments the particles are activated carbon.

It will be appreciated that more than one type of particle is easily incorporated into the webs of the invention by providing a particle mix in the volumetric screw feeder; or by providing more than one feeder supplying particles to the flow of polymer solution. In this way, different particles are easily incorporated into the web.

Various embodiments allow use of a web comprising fine fiber and reactive, adsorptive or absorptive, inert or chemically modified particulates. Chemical modification is in the form of chemical or thermal treatment of the polymers, fibers and/or particulates or in the form of chemical impregnation of the particulates. It also includes mixing impregnates within the fiber/particulate web. Fluid passing through the web (typically a gas) interacts with the chemically- or thermally-modified web constituents. The active particulates can react with, absorb, or adsorb a portion of the fluid. It can allow selective chemical reactions of particular compounds or species in the fluid with other compounds or species attracted to or trapped on the surface. The surface of the particulates can also play the role of a catalyst through providing active sites that catalytically alter the material that passes through the web.

The particulates may be impregnated with a single or several impregnates, such as impregnation of activated carbon with sodium hydroxide alone for $H_2S$ removal or impregnation of a mixture of sodium hydroxide and potassium iodide. This latter composition has a higher adsorption capacity and efficiency for removal of $H_2S$ than activated carbon impregnated with sodium hydroxide. It is believed that the potassium iodide enhances the action of the sodium hydroxide catalytically or synergistically. Potassium iodide plays the role of oxidant which promotes oxidation of $H_2S$ to sulfur. In this particular case, the concepts taught herein can be applied as ostomy bag filters for $H_2S$ removal where the web with its constituents in this invention will provide the conditions required for ostomy bag filters such as low flow, low pressure drop, high $H_2S$ capacity. Other usable impregnates include citric acid, potassium hydroxide, potassium carbonate, sodium carbonate, potassium bicarbonate, sodium bicarbonate, and/or moisture, among others. Those compounds can be either impregnated on the particulates or mixed with the web constituents.

A few examples of impregnates on activated carbons and their applications include: Activated carbons impregnated with potassium carbonate for the removal of acid gases (HCl, HF, $SO_2$, $H_2S$, $NO_2$); activated carbons impregnated with potassium iodide for the removal of $H_2S$ and $PH_3$; activated carbons impregnated with iron oxide for the removal of $H_2S$ and mercaptan; and activated carbons impregnated with potassium permanganate for the removal of $H_2S$ from oxygen-lacking gases. The use of a combination of particulates with different impregnates within the web for different applications is also appropriate in certain implementations. For example, it is possible to use of a mixture of two activated carbons.

The presence of water enhances $H_2S$ removal in combination with many of the above specified impregnates. Water can be stored on the carbon surface or within the web through pre-humidification or through the use of impregnates or additional adsorbents that attract water vapor to their surfaces during the application. Several types of adsorbents can be used to cover the desired ranges of humidity and they include molecular sieves, activated alumina, silica gel and activated carbons. These adsorbent materials can be further modified by oxidation, heating, or impregnation. Impregnation is commonly done with alkali metals sulfate, citric acid, alkali metals carbonates, alkali metals bicarbonates, lithium and sodium chlorides, calcium chloride, and/or a mixture thereof.

It is also possible to add water adsorbent particles that will be capable of picking up water at low humidity or storing it. These water adsorbent particles can release some of their humidity in dry conditions. The presence of the released water can then enhance $H_2S$ removal in dry conditions.

Besides using particles that have been impregnated or coated with reactive species, it should be apparent that these modifications can be performed after forming the fibrous web and structures. Imparting reactive activity to the particles and web after forming the fibrous web and structure can be accomplished using various different coating processes. For example, spray coating, dip coating, aerosol deposition, chemical vapor deposition, and vacuum coating. A final step can involve a drying process that may, or may not, include thermal treatments, gas purging, or vacuum methods.

Furthermore, the chemistry of the walls of the first layer can be made to adsorb acidic, basic, and organic and water vapors, as well as several specific classes of compounds including reactive carbonyl compounds, such as formaldehyde, acetaldehyde and acetone. The reactive materials can be held together with adhesive or fibers to encapsulate, or simply hold, the particles. Also, additional scrim materials can be attached to hold the reactive material in place and minimize shedding of particles. The reactive material can also be sandwiched between layers of scrim. The scrim can help to produce the channels or space between the layers. This can be accomplished with a high loft scrim material that gives the proper spacing as well as ability to hold all the reactive particles in the media.

Additional Functional Layers

It can also be advantageous to provide one or more additional functional layers to the webs besides the nonwoven fine fiber composite webs. A functional layer can be a coating or a separately formed layer of material. For example, microporous layers, foam layers, expanded polytetrafluoroethylene layers, water repellent layers or coatings, odor masking layers or coatings, or a combination thereof may be provided on one or both sides of the nonwoven fine fiber composite webs of the invention.

Such additional layers can add additional functionality to the web when that functionality is not practical to build into the web as it is formed. For example, for providing adhesion of the web onto a substrate, it may be desirable not to provide a fluorochemical coating to the web. But where oil repellency is desirable in the application, fluorochemicals provide the requisite protection.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A filter assembly for venting gas from an ostomy bag comprising:

a first layer configured to be gas permeable and liquid impermeable;

an adhesive layer defining at least a first adhesive layer opening;

an adsorbent element comprising a gas-adsorbing material, the adsorbent element disposed between the first layer and the adhesive layer;

a barrier layer disposed between the first layer and the adsorbent element, wherein the barrier layer is gas impermeable; and a second layer comprising a material having a melt temperature at or below 120° C. and defining at least a first opening in the second layer, the second layer configured to be welded to the ostomy bag at an annular weld area surrounding the first opening in the second layer;

wherein the adhesive layer is configured to adhere to the first layer, the adsorbent element, and the second layer, such that the first adhesive layer opening overlaps with the first opening in the second layer;

wherein the filter assembly is configured such that, when the filter assembly is welded over an exit opening of the ostomy bag, gas from within the ostomy bag enters the adsorbent element where the barrier layer is not present, flows laterally through the adsorbent element, and exits the filter assembly through the first opening in the second layer; and wherein perimeters of the first layer, the adhesive layer, and the second layer are substantially aligned.

2. The filter assembly of claim 1, the first layer comprising one of a group consisting of polytetrafluoroethylene (PTFE) and a PTFE laminate.

3. The filter assembly of claim 1, the adhesive layer comprising one of a group consisting of double-sided adhesive laminate and a pressure sensitive adhesive.

4. The filter assembly of claim 1, wherein the adhesive layer is a coating on the second layer.

5. The filter assembly of claim 1, the adsorbent element comprising activated carbon.

6. The filter assembly of claim 1, the second layer comprising ethylene-vinyl acetate (EVA), polyethylene (PE), or polypropylene (PP).

7. The filter assembly of claim 1, wherein the first and second openings overlap at least about 70% of a length of the adsorbent element.

8. The filter assembly of claim 1, wherein the first and second openings overlap at least about 25% of an area of one side of the adsorbent element.

9. The filter assembly of claim 1, wherein the adhesive layer further defines a third opening and the second layer further defines a fourth opening that overlaps with the third opening.

10. The filter assembly of claim 9, wherein the overlapped first and second opening define a first filter assembly opening, wherein the overlapped third and fourth openings define a second filter assembly opening, and wherein the first and second filter assembly openings are substantially equal in area.

11. The filter assembly of claim 1, wherein the adhesive layer defines at least the first adhesive layer opening and a second adhesive layer opening, and wherein the second layer defines at least the first opening in the second layer and a second opening in the second layer.

12. The filter assembly of claim 11, wherein the adhesive layer is configured to adhere to the first layer, the adsorbent element, and the second layer, such that the first adhesive layer opening overlaps with the first opening in the second layer and the second adhesive layer opening overlaps with the second opening in the second layer.

13. The filter assembly of claim 11, wherein the adhesive layer is configured to adhere to the first layer, the adsorbent element, and the second layer, such that an inner edge of the first adhesive layer opening is aligned with an inner edge of the first opening in the second layer and an inner edge of the second adhesive layer opening is aligned with an inner edge of the second opening in the second layer.

14. The filter assembly of claim 1, wherein the filter assembly is configured such that, when the filter assembly is welded over an exit opening of the ostomy bag, gas from within the ostomy bag enters the adsorbent element at an outer edge of the adsorbent element that is perpendicular to the second layer.

\* \* \* \* \*